United States Patent [19]
Doll et al.

[11] Patent Number: 5,945,430
[45] Date of Patent: Aug. 31, 1999

[54] AMINOOXYAMIDE TRICYCLIC INHIBITORS OF FARNESYL-PROTEIN TRANSFERASE

[75] Inventors: Ronald J. Doll, Maplewood; Tarik Lalwani, Edison, both of N.J.

[73] Assignee: Schering Corporation, Kenilworth, N.J.

[21] Appl. No.: 09/094,685

[22] Filed: Jun. 15, 1998

Related U.S. Application Data

[60] Provisional application No. 60/049,957, Jun. 17, 1997.

[51] Int. Cl.$^6$ .................... A61K 31/44; C07D 401/04; C07D 401/14
[52] U.S. Cl. .................... 514/290; 546/93
[58] Field of Search .................... 546/93; 514/290

[56] References Cited

U.S. PATENT DOCUMENTS

| | | | |
|---|---|---|---|
| 5,438,062 | 8/1995 | Piwinski et al. | 514/290 |
| 5,665,726 | 9/1997 | Piwinski et al. | 514/290 |
| 5,696,121 | 12/1997 | Bishop | 514/254 |

FOREIGN PATENT DOCUMENTS

| | | |
|---|---|---|
| 0270 818 A1 | 6/1988 | European Pat. Off. . |
| WO 9510516 | 4/1995 | WIPO . |
| WO 96/30363 | 10/1996 | WIPO . |

OTHER PUBLICATIONS

Khosravi–Far R et al. Cell Growth & Differentiation. 3, 461–9, Jul. 1992.

*Primary Examiner*—Evelyn Mei Huang
*Attorney, Agent, or Firm*—Joseph T. Majka

[57] ABSTRACT

Novel aminooxyamide tricyclic compounds and pharmaceutical compositions are disclosed which are inhibitors of the enzyme, farnesyl protein transferase. Also disclosed is a method of inhibiting Ras function and therefore inhibiting the abnormal growth of cells. The method comprises administering the novel aminooxyamide tricyclic compound to a biological system. In particular, the method inhibits the abnormal growth of cells in a mammals such as a human.

21 Claims, No Drawings

AMINOOXYAMIDE TRICYCLIC INHIBITORS OF FARNESYL-PROTEIN TRANSFERASE

This application claims the benefit of provisional application No. 60/049957, filed Jun. 17, 1997.

BACKGROUND

Patent application WO 95/00497 published Jan. 5, 1995 under the Patent Cooperation Treaty (PCT) describes compounds which inhibit the enzyme, farnesyl-protein transferase (FTase) and the farnesylation of the oncogene protein Ras. Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be additional compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Compounds useful in the claimed methods are represented by Formula 1.0:

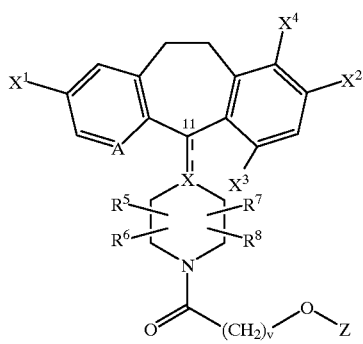

(1.0)

or a pharmaceutically acceptable salt or solvate thereof, wherein:

A represents N or N-oxide;

X represents N, CH or C, such that when X is N or CH, there is a single bond to carbon atom 11 as represented by the solid line; or when X is C, there is a double bond to carbon atom 11, as represented by the solid and dotted lines;

$X^1$ and $X^2$ are independently selected from bromo, iodo or chloro;

$X^3$ and $X^4$ are independently selected from bromo, iodo, chloro or hydrogen provided only one of $X^3$ or $X^4$ is hydrogen;

$R^5$, $R^6$, $R^7$ and $R^8$ each independently represents hydrogen, alkyl, aryl, or —$CONR^{40}R^{41}$ wherein $R^{40}$ and $R^{41}$ independently represent hydrogen, alkyl, alkoxy, aryl, aralkyl, heteroaryl, heteroarylalkyl, cycloalkyl, cycloalkylalkyl, heterocycloalkyl and heterocycloalkylalkyl, and further wherein $R^5$ may be combined with $R^6$ to represent =O or =S and/or $R^7$ may be combined with $R^8$ to represent =O or =S;

v is 1, 2, 3, 4, 5 or 6;

Z represents —$NR^{19}R^{20}$ or —$N=CR^{19}R^{20}$; wherein $R^{19}$ and $R^{20}$ are independently selected from hydrogen, alkyl, alkoxy, aryl, aralkyl, heteroaryl, heteroarylalkyl, cycloalkyl, cycloalkylalkyl, heterocycloalkyl, heterocycloalkylalkyl, —$CONR^{10}R^{12}$, —$COOR^{10}$, —$COR^{10}$, —$SO_2R^{10}$ and —$SO_2NR^{10}R^{12}$, or $R^{19}$ and $R^{20}$ taken together can form a cycloalkyl or a heterocycloalkyl ring, wherein $R^{10}$ and $R^{12}$ are independently selected from hydrogen, alkyl, alkoxy, aryl, aralkyl, heteroaryl, heteroarylalkyl, cycloalkyl, cycloalkylalkyl, heterocycloalkyl or heterocycloalkylalkyl.

Preferably in compound (1.0), there is a single bond at carbon atom 11; X is CH; $R^5$, $R^6$, $R^7$ and $R^8$ are hydrogen; $X^1$, $X^2$ and $X^3$ are bromo or chloro and $X^4$ is hydrogen; v is one or two; and Z is —$NR^{19}R^{20}$ or —$N=CR^{19}R^{20}$ wherein $R^{19}$ and $R^{20}$ are independently selected from hydrogen, alkyl, aryl, heteroaryl, —$COR^{10}$ or —$COOR^{10}$ wherein $R^{10}$ is hydrogen or alkyl, or $R^{19}$ and $R^{20}$ taken together form a cycloalkyl or a heterocycloalkyl ring. When $R^{20}$ is aryl, an optional substituent on the aryl ring may be alkoxy, hydroxy or halo. When $R^{19}$ and $R^{20}$ taken together form a cycloalkyl ring, an optional substituent on the cycloalkyl ring is heterocycloalkyl. Preferred compounds include those of Examples 1, 2, 4, 6, 10, 11, 12, 13, 14 and 15.

In another embodiment, the present invention is directed toward a pharmaceutical composition for inhibiting the abnormal growth of cells comprising an effective amount of compound (1.0) in combination with a pharmaceutically acceptable carrier.

In another embodiment, the present invention is directed toward a method for inhibiting the abnormal growth of cells, including transformed cells, comprising administering an effective amount of compound (1.0) to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs, and (4) benign or malignant cells that are activated by mechanisms other than the Ras protein. Without wishing to be bound by theory, it is believed that these compounds may function either through the inhibition of G-protein function, such as ras p21, by blocking G-protein isoprenylation, thus making them useful in the treatment of proliferative diseases such as tumor growth and cancer, or through inhibition of ras farnesyl protein transferase, thus making them useful for their antiproliferative activity against ras transformed cells.

The cells to be inhibited can be tumor cells expressing an activated ras oncogene. For example, the types of cells that may be inhibited include pancreatic tumor cells, lung cancer cells, myeloid leukemia tumor cells, thyroid follicular tumor cells, myelodysplastic tumor cells, epidermal carcinoma tumor cells, bladder carcinoma tumor cells, prostate tumor cells, breast tumor cells or colon tumors cells. Also, the inhibition of the abnormal growth of cells by the treatment with compound (1.0) may be by inhibiting ras farnesyl protein transferase. The inhibition may be of tumor cells wherein the Ras protein is activated as a result of oncogenic mutation in genes other than the Ras gene. Alternatively, compounds (1.0) may inhibit tumor cells activated by a protein other than the Ras protein.

This invention also provides a method for inhibiting tumor growth by administering an effective amount of compound (1.0) to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, mnyelodysplastic syndrome (MDS), bladder carcinoma, prostate carcinoma and breast carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the N-substituted urea compounds (1.0) described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the N-substituted urea compounds (1.0).

In another embodiment, the present invention is directed toward a method for inhibiting ras farnesyl protein transferase and the farnesylation of the oncogene protein Ras by administering an effective amount of compound (1.0) to mammals, especially humans. The administration of the compounds of this invention to patients, to inhibit farnesyl protein transferase, is useful in the treatment of the cancers described above.

DETAILED DESCRIPTION OF THE INVENTION

As used herein, the following terms are used as defined below unless otherwise indicated:

$M^+$—represents the molecular ion of the molecule in the mass spectrum;

$MH^+$—represents the molecular ion plus hydrogen of the molecule in the mass spectrum;

Bu—represents butyl;

Et—represents ethyl;

Me—represents methyl;

Ph—represents phenyl;

benzotriazol-1-yloxy represents

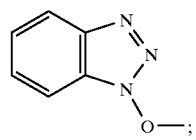

1-methyl-tetrazol-5-ylthio represents

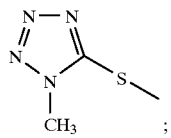

alkyl—(including the alkyl portions of alkoxy, alkylamino and dialkylamino)—represents straight and branched carbon chains and contains from one to twenty carbon atoms, preferably one to six carbon atoms; for example methyl, ethyl, propyl, iso-propyl, n-butyl, t-butyl, n-pentyl, isopentyl, hexyl and the like; wherein said alkyl group may be optionally and independently substituted with one, two, three or more of the following: halo, alkyl, aryl, cycloalkyl, cyano, —$CF_3$, oxy (═O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ can independently represent hydrogen, alkyl, alkoxy, aryl, aralkyl, heteroaryl, heteroarylalkyl, cycloalkyl, cycloalkylalkyl, heterocycloalkyl or heterocycloalkylalkyl;

alkenyl—represents straight and branched carbon chains having at least one carbon to carbon double bond and containing from 2 to 12 carbon atoms, preferably from 2 to 6 carbon atoms and most preferably from 3 to 6 carbon atoms; wherein said alkenyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

alkoxy—an alkyl moiety of one to 20 carbon atoms covalently bonded to an adjacent structural element through an oxygen atom, for example, methoxy, ethoxy, propoxy, butoxy, pentoxy, hexoxy and the like; wherein said alkoxy group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

aryl (including the aryl portion of aralkyl)—represents a carbocyclic group containing from 6 to 15 carbon atoms and having at least one aromatic ring (e.g., aryl is phenyl), wherein said aryl group optionally can be fused with aryl, cycloalkyl, heteroaryl or heterocycloalkyl rings; and wherein any of the available substitutable carbon and nitrogen atoms in said aryl group and/or said fused ring(s) may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

aralkyl—represents an alkyl group, as defined above, wherein one or more hydrogen atoms of the alkyl moiety have been substituted with one or more aryl groups; wherein said aralkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

aryloxy—represents an aryl group, as defined above, wherein said aryl group is covalently bonded to an adjacent structural element through an oxygen atom, for example, phenoxy, wherein said aryl group optionally can be fused with aryl, cycloalkyl, heteroaryl or heterocycloalkyl rings; and wherein any of the available substitutable carbon and nitrogen atoms in said aryloxy group and/or said fused ring(s) may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

cycloalkyl—represents saturated carbocyclic rings branched or unbranched of from 3 to 20 carbon atoms, preferably 3 to 7 carbon atoms; wherein said cycloalkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

cycloalkylalkyl—represents an alkyl group, as defined above, wherein one or more hydrogen atoms of the alkyl moiety have been substituted with one or more cycloalkyl groups; wherein said cycloalkylalkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$OCOR^{10}$, —$OCO_2R^{10}$ or —$COOR^{10}$, wherein $R^{10}$ and $R^{12}$ are as defined hereinabove;

halo—represents fluoro, chloro, bromo and iodo;

heteroalkyl—represents straight and branched carbon chains containing from one to twenty carbon atoms, preferably one to six carbon atoms interrupted by 1 to 3 heteroatoms selected from —O—, —S— and —N—; wherein any of the available substitutable carbon and nitrogen atoms in said heteroalkyl chain may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

heteroaryl—represents cyclic groups having at least one heteroatom selected from O, S and N, said heteroatom (s) interrupting a carbocyclic ring structure and having a sufficient number of delocalized pi electrons to provide aromatic character, with the aromatic heterocyclic groups containing from 2 to 14 carbon atoms,wherein said heteroaryl group optionally can be fused with one or more aryl, cycloalkyl, heteroaryl or heterocycloalkyl rings; and wherein any of the available substitutable carbon or nitrogen atoms in said heteroaryl group and/or said fused ring(s) may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove.

Representative heteroaryl groups can include, for example, furanyl, imidazoyl, pyrimidinyl, triazolyl, 2-, 3- or 4-pyridyl or 2-, 3- or 4-pyridyl N-oxide wherein pyridyl N-oxide can be represented as:

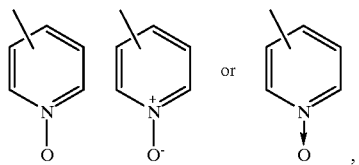

heteroarylalkyl—represents an alkyl group, as defined above, wherein one or more hydrogen atoms have been replaced by one or more heteroaryl groups; wherein said heteroarylalkyl group may be optionally and independently substituted with one, two, three or more of the following: halo, alkyl, aryl, cycloalkyl, cyano, —$CF_3$, oxy (=O), aryloxy, —$OR^{10}$, —$OF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove;

heterocycloalkyl—represents a saturated, branched or unbranched carbocylic ring containing from 3 to 15 carbon atoms, preferably from 4 to 6 carbon atoms, which carbocyclic ring is interrupted by 1 to 3 heteroatoms selected from —O—, —S— and —N—, wherein optionally, said ring may contain one or two unsaturated bonds which do not impart aromatic character to the ring; and wherein any of the available substitutable carbon and nitrogen atoms in the ring may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove. Representative heterocycloalkyl groups can include 2- or 3-tetrahydrofuranyl, 2- or 3-tetrahydrothienyl, 1-, 2-, 3- or 4-piperidinyl, 2- or 3-pyrrolidinyl, 1-, 2- or 3-piperizinyl, 2- or 4-dioxanyl, morpholinyl,

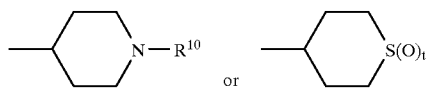

wherein $R^{10}$ is defined hereinbefore and t is 0, 1 or 2.

heterocycloalkalkyl—represents an alkyl group, as defined above, wherein one or more hydrogen atoms have been replaced by one or more heterocycloalkyl groups; wherein optionally, said ring may contain one or two unsaturated bonds which do not impart aromatic character to the ring; and wherein said heterocycloalkylalkyl group may be optionally and independently substituted with one, two, three or more of the following: halo, alkyl, aryl, cycloalkyl, cyano, —$CF_3$, oxy (=O), aryloxy, —$OR^{10}$, —$OCF_3$, heterocycloalkyl, heteroaryl, —$NR^{10}R^{12}$, —$NHSO_2R^{10}$, —$SO_2NH_2$, —$SO_2NHR^{10}$, —$SO_2R^{10}$, —$SOR^{10}$, —$SR^{10}$, —$NHSO_2$, —$NO_2$, —$CONR^{10}R^{12}$, —$NR^{12}COR^{10}$, —$COR^{10}$, —$OCOR^{10}$, —$OCO_2R^{10}$ or —$COOR^{10}$, wherein $R^{10}$ and $R^{12}$ are as defined hereinabove.

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine ($Et_3N$); diethyl ether ($Et_2O$); ethyl chloroformate ($ClCO_2Et$); 1-(3-dimethylaminopropyl)-3-ethyl carbodiimide hydrochloride (DEC); and dicyclohexylcarbodiimide (DCC).

Reference to the position of the substituents $X^1$, $X^2$, $X^3$ and $X^4$ is based on the numbered ring structure:

(1.0)

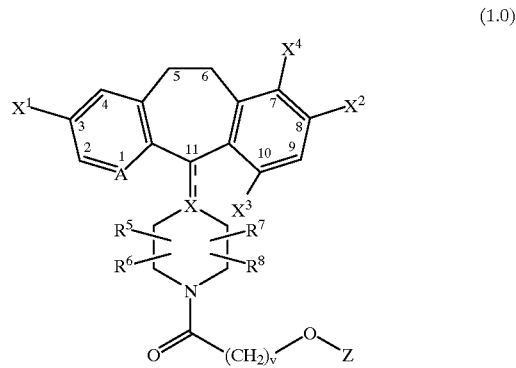

Certain compounds of the invention may exist in different stereoisomeric forms (e.g., enantiomers, diastereoisomers and atropisomers). The invention contemplates all such stereoisomers both in pure form and in mixture, including racemic mixtures. For example, the carbon atom at the C-11 position can be in the S or R stereoconfiguration.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purpopses of the invention.

Compounds of the present invention can be prepared according to the following Scheme I:

Scheme I

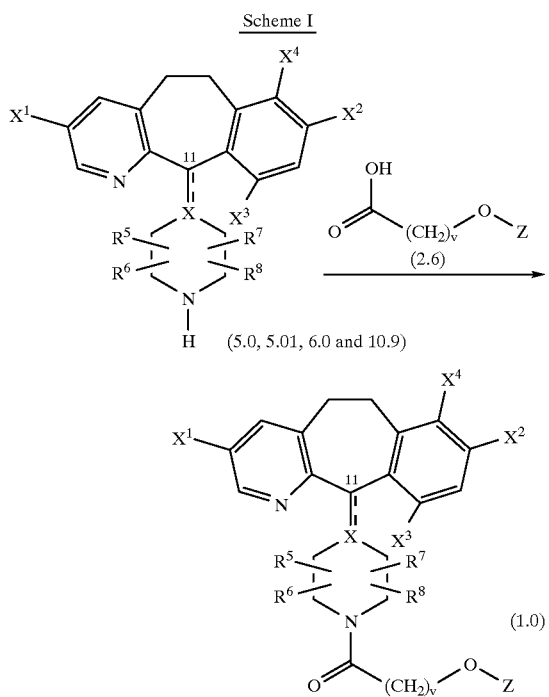

wherein $X, X^1, X^2, X^3, X^4, R^5, R^6, R^7, R^8$, v, Z and the solid and dotted lines are as defined hereinbefore.

Referring to the Scheme I, compounds of formula (1.0) can be prepared by reacting the tricyclic amine compounds (5.0, 5.01, 6.0 and 10.9) with the corresponding aminooxy acid of formula (2.6), preferably using a carbodiimide coupling reagent such as DEC or DCC, in a protic or aprotic solvent such as water, DMF, methanol or ethanol, at temperatures ranging from 0° to 100° C., preferably at about 25° C. The amount of the aminooxy acid (2.6) in the reaction mixture can range from 1 to 10 moles per mole of tricyclic amine compounds (5.0, 5.01, 6.0 and 10.9), preferably with equimolar amounts of aminooxy acid (2.6). About an equimolar amount of the coupling agent can be used per mole of aminooxy acid (2.6).

Compounds of fomula (1.0) can be isolated from the reaction mixture using conventional procedures, such as, for example, extraction of the reaction mixture from water with organic solvents, evaporation of the organic solvents, followed by chromatography on silica gel or other suitable chromatographic media. Alternatively, compounds (1.0) can be dissolved in a water-miscible solvent, such as methanol, the methanol solution is added to water to precipitate the compound, and the precipitate is isolated by filtration or centrifugation.

(+)-Isomers of compounds of formula (5.0, 6.0 and 10.9) wherein X is CH can be prepared with high enantioselectivity by using a process comprising enzyme catalyzed transesterification. Preferably, a racemic compound of formula (5.0, 6.0 and 10.9), wherein X is C, the double bond is present and $X^3$ is not H, is reacted with an enzyme such as Toyobo LIP-300 and an acylating agent such as trifluoroethly isobutyrate; the resultant (+)-amide is then hydrolyzed, for example by refluxing with an acid such as $H_2SO_4$, to obtain the corresponding optically enriched (+)-isomer wherein X is CH and $R^3$ is not H. Alternatively, a racemic compound of formula (5.0, 6.0 and 10.9), wherein X is C, the double bond is present and $R^3$ is not H, is first reduced to the corresponding racemic compound of formula (5.0, 6.0 and 10.9) wherein X is CH and then treated with the enzyme (Toyobo LIP-300) and acylating agent as described above to obtain the (+)-amide, which is hydrolyzed to obtain the optically enriched (+)-isomer.

Compounds of the present invention and preparative starting materials therof, are exemplified by the following examples, which should not be construed as limiting the scope of the disclosure.

EXAMPLE 1

(+)-N-[2-[4-(3,10-dibromo-8-chloro-6,11-dihydro-5H-benzo[5,6]cyclohepta[1,2-b]pyridin-11(R)-yl))-1-piperidinyl]-2-oxoethoxy]benzamide

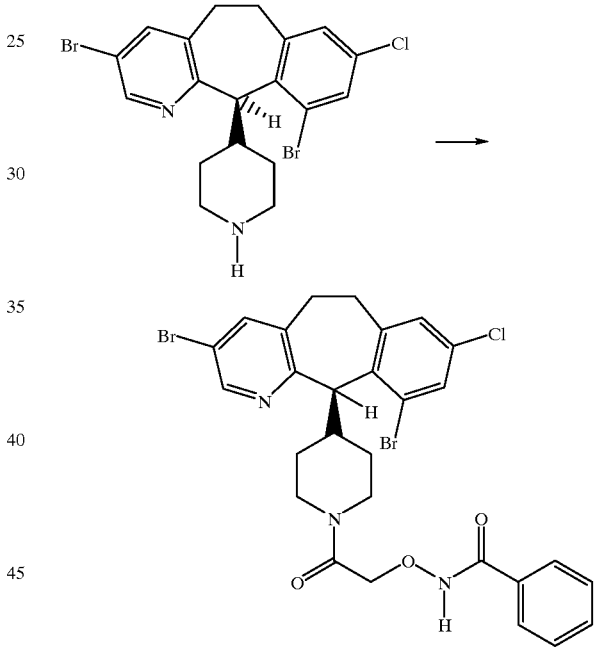

Dissolve the (+) isomer of Preparative Example 3, (0.2 g, 0.43 mmol) in 3 mL of DMF, stir at room temperature and add 0.056 g (0.55 mmol) of 4-methylmorpholine, 0.106 g (0.55 mmol) of DEC, 0.75 g (0.55 mmol) of HOBT and 0.108 g (0.55 mmole) of N-benzoylaminooxyacetic acid (Salor). Stir the mixture at room temperature for 18 hr, then concentrate in vacuo to a residue and partition between ethyl acetate and water. Wash the organic phase with aqueous sodium bicarbonate solution then brine. Dry the organic phase over magnesium sulfate, filter and concentrate in vacuo to a residue. Chromatograph the residue on silica gel, eluting with dichloromethane (saturated with ammonia)—methanol (95%–5%) to yield the title compound (0.2 g) as a white solid. M.p.=212°–222° C., Mass Spec.: MH+=647. $[\alpha]_D^{24.6° C.}=+44.2°$, c=0.08, methanol.

EXAMPLE 2

(+)-4-(3,10-dibromo-8-chloro-6,11-dihydro-5H-benzo[5,6]cyclohepta[1,2-b]pyridin-11(R)-yl)]-1-[[[(1-methylethylidene)amino]oxy]acetyl]piperidine

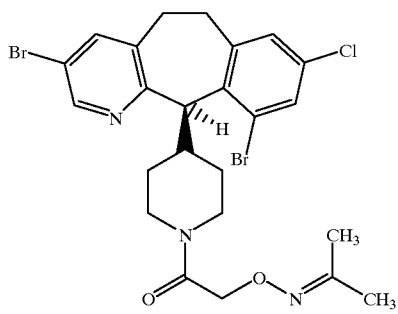

The title compound is prepared following essentially the same procedure as described in Example 1 except that the carboxylic acid of Preparative Example 11 is used instead of N-benzoylaminooxyacetic acid, to obtain the title compound, mp=98° C.

EXAMPLE 3

(+)-4-(3,10-dibromo-8-chloro-6,11-dihydro-5H-benzo[5,6]cyclohepta[1,2-b]pyridin-11(R)-yl))-1-[[[(1-(4-methoxyphenyl)ethylidene]amino]oxy]acetyl]piperidine

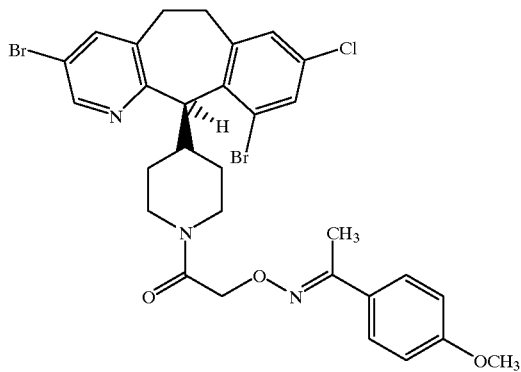

The title compound is prepared following essentially the same procedure as described in Example 1 except that 4-methoxyphenyl-ethylidene aminooxyacetic acid is used instead of N-benzoylaminooxyacetic acid, to obtain the title compound, mp=101–108 (d)° C.

EXAMPLE 4

(+)-4-(3,10-dibromo-8-chloro-6,11-dihydro-5H-benzo[5,6]cyclohepta[1,2-b]pyridin-11(R)-yl)-1-[3-[[(1-methylethylidene]amino]oxy]-1-oxopropyl]piperidine, 0.17 hydrate

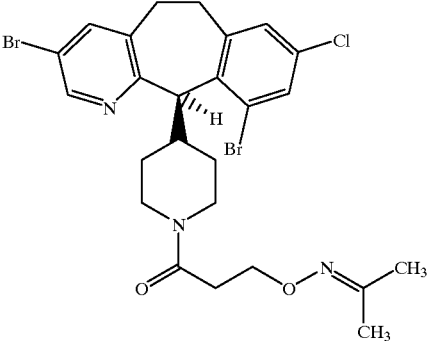

The title compound is prepared following essentially the same procedure as described in Example 1 except that the carboxylic acid of Preparative Example 12 is used instead of N-benzoylaminooxyacetic acid, to obtain the title compound, mp=90–98° C.

EXAMPLE 5

(+)-1,1-Dimethylethyl-N-[2-[4-(3,10-dibromo-8-chloro-6,11-dihydro-5H-benzo[5,6]cyclohepta[1,2-b]pyridin-11(R)-yl)-1-piperidinyl]-2-oxoethoxy]carbamate, 0.4 hydrate

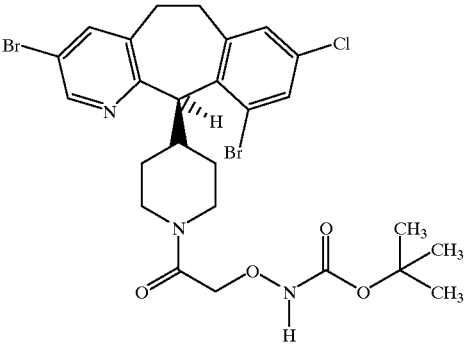

The title compound is prepared following essentially the same procedure as described in Example 1 except that the carboxylic acid of Preparative Example 19 is used instead of N-benzoylaminooxyacetic acid, to obtain the title compound, mp=137–141° C.

EXAMPLE 6

(+)-4-(3,10-dibromo-8-chloro-6,11-dihydro-5H-benzo[5,6]cyclohepta[1,2-b]pyridin-11(R)-yl)-1-[[[(E)-4-pyridinylmethylene)amino]oxy]acetyl]piperidine N1-oxide

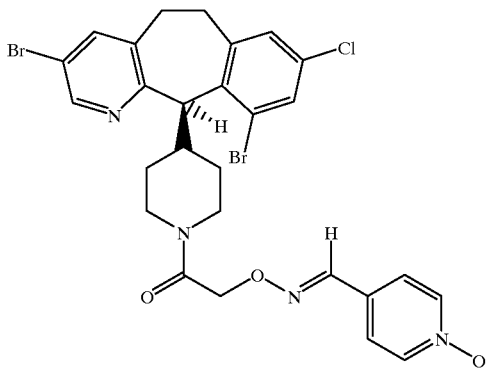

The title compound is prepared following essentially the same procedure as described in Example 1 except that the carboxylic acid of Preparative Example 13 is used instead of N-benzoylaminooxyacetic acid, to obtain the title compound, mp=128–140 (d)° C. COS(IC$_{50}$)=0.69 μM.

EXAMPLE 7

(+)-4-(3,10-dibromo-8-chloro-6,11-dihydro-5H-benzo[5,6]cyclohepta[1,2-b]pyridin-11(R)-yl)-1-[[[(E)-4-2-hydroxyphenyl)methylene]amino]oxy]acetyl]piperidine

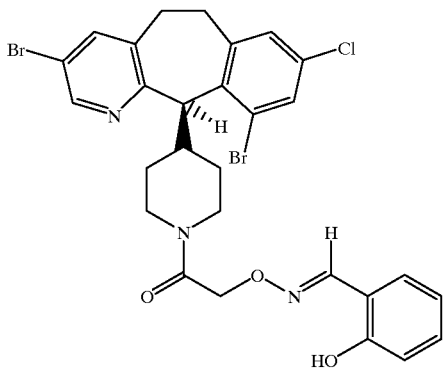

The title compound is prepared following essentially the same procedure as described in Example 1 except that the carboxylic acid of Preparative Example 14 is used instead of N-benzoylaminooxyacetic acid, to obtain the title compound, mp=124–129 (d)° C.

EXAMPLE 8

(+)-1-[[[[(E)-1-(4-chlorophenyl)ethylidene]amino]oxy]acetyl]-4-(3,10-dibromo-8-chloro-6,11-dihydro-5H-benzo[5,6]cyclohepta[1,2-b]pyridin-11(R)-yl)piperidine

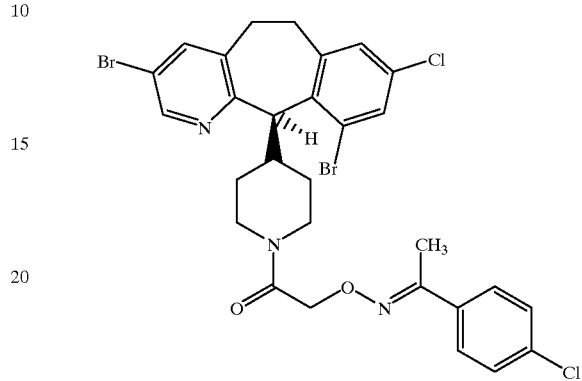

The title compound is prepared following essentially the same procedure as described in Example 1 except that 4-chlorophenylethylideneaminooxy acetic acid is used instead of N-benzoylaminooxyacetic acid, to obtain the title compound, mp=120–129° C.

EXAMPLE 9

(+)-4-(3,10-dibromo-8-chloro-6,11-dihydro-5H-benzo[5,6]cyclohepta[1,2-b]pyridin-11(R)-yl)-1-[[[[(E)-1-(2-thienyl)ethylidene]amino]oxy]acetyl]piperidine

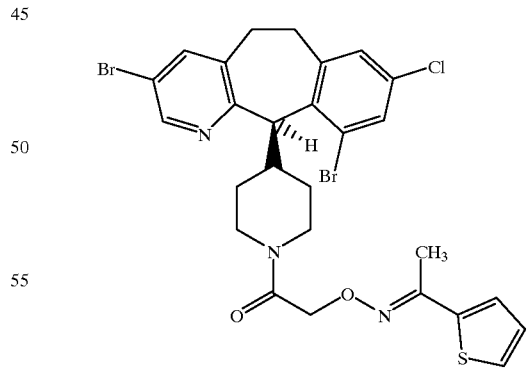

The title compound is prepared following essentially the same procedure as described in Example 1 except that 2-thienylethylideneaminooxy acetic acid is used instead of N-benzoylaminooxyacetic acid, to obtain the title compound, mp=112–122 (d)° C.

EXAMPLE 10

(+)-4-(3,10-dibromo-8-chloro-6,11-dihydro-5H-benzo[5,6]cyclohepta[1,2-b]pyridin-11(R)-yl)-1-[[[[(cyclohexylidene]amino]]oxy]acetyl]piperidine

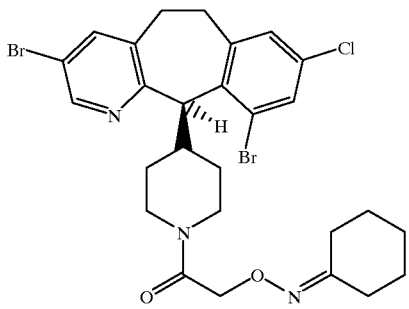

The title compound is prepared following essentially the same procedure as described in Example 1 except that the carboxylic acid of Preparative Example 15 is used instead of N-benzoylaminooxyacetic acid, to obtain the title compound, mp=95–100 (d)° C.

EXAMPLE 11

(+)-4-(3,10-dibromo-8-chloro-6,11-dihydro-5H-benzo[5,6]cyclohepta[1,2-b]pyridin-11(R)-yl)-1-[[[[1,4-dioxospiro[4.5]decan-8-ylidene]amino]oxy]acetyl]piperidine

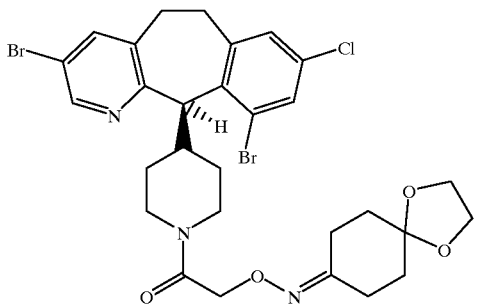

The title compound is prepared following essentially the same procedure as described in Example 1 except that the carboxylic acid of Preparative Example 16 is used instead of N-benzoylaminooxyacetic acid, to obtain the title compound, mp=115–121 (d)° C.

EXAMPLE 12

(+)-4-(3,10-dibromo-8-chloro-6,11-dihydro-5H-benzo[5,6]cyclohepta[1,2-b]pyridin-11(R)-yl)-1-[[[[(tetrahydro-4H-pyran-4-ylidene]amino]oxy]acetyl]piperidine

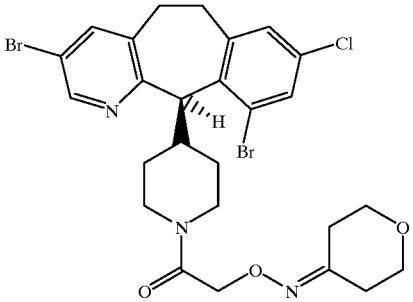

The title compound is prepared following essentially the same procedure as described in Example 1 except that the carboxylic acid of Preparative Example 17 is used instead of N-benzoylaminooxyacetic acid, to obtain the title compound, mp=119–128° C.

EXAMPLE 13

(+)-4-(3,10-dibromo-8-chloro-6,11-dihydro-5H-benzo[5,6]cyclohepta[1,2-b]pyridin-11(R)-yl)-1-[[[[(tetrahydro-4H-thiopyran-4-ylidene]amino]oxy]acetyl]piperidine

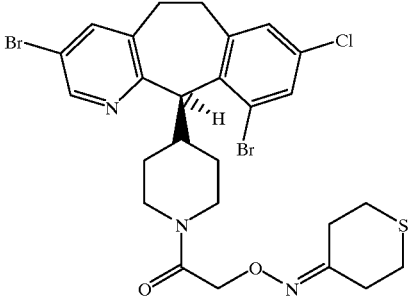

The title compound is prepared following essentially the same procedure as described in Example 1 except that the carboxylic acid of Preparative Example 18 is used instead of N-benzoylaminooxyacetic acid, to obtain the title compound, mp=117–123° C.

EXAMPLE 14

(+)-N-[2-[4-(3,10-dibromo-8-chloro-6,11-dihydro-5H-benzo[5,6]cyclohepta[1,2-b]pyridin-11(R)-yl)-1-piperidinyl]-2-oxoethoxy]acetamide

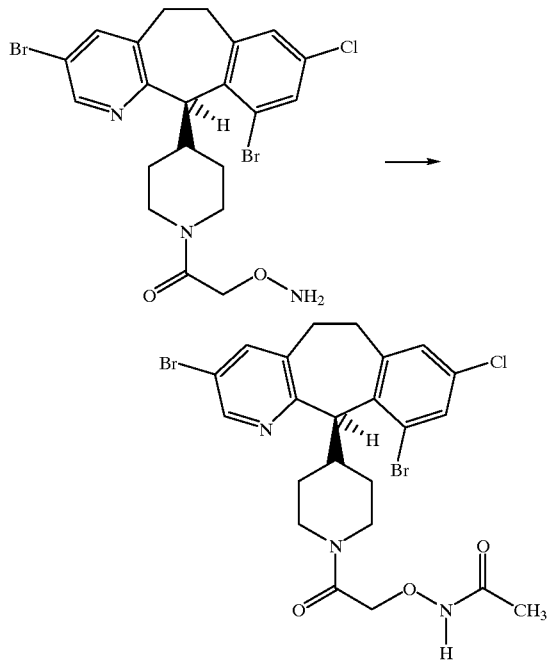

Dissolve 0.06 g (0.103 mmol) of the product of Example 15 in 1.5 mL of pyridine and add 0.018 g (0.181 mmol) of acetic anhydride. After 1 hour, concentrate under vacuum and partition the residue between ethyl acetate and aqueous sodium bicarbonate solution. Dry the organic layer over magnesium sulfate and concentrate under vacuum to obtain the product as a white solid, mp=108–117 (d)° C.

EXAMPLE 15

(+)-1-[(aminooxy)acetyl]-4-(3,10-dibromo-8-chloro-6,11-dihydro-5H-benzo[5,6]cyclohepta[1,2-b]pyridin-11(R)-yl)piperidine

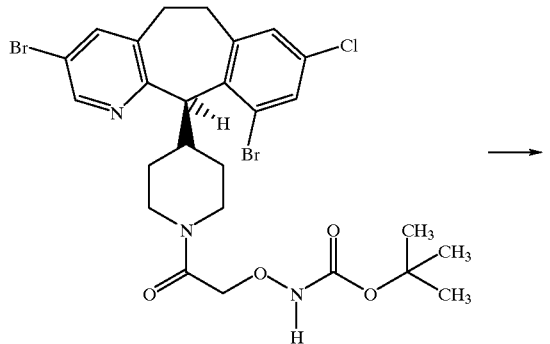

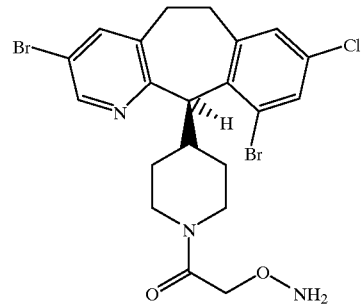

Dissolve 0.170 g (0.264 mmol) of the title compound of Example 5 in 10 mL of dioxane saturated with HCl gas. After 1 hour, concentrate under vacuum and triturate the residue with ethyl ether to give the hydrochloride salt of the product as a white solid, m.p.=178–192(d)° C.

PREPARATION OF STARTING MATERIALS

Starting materials useful in preparing the compounds of the present invention are exemplified by the following preparative examples, which should not be construed to limit the scope of the disclosure. The aminooxy acids of formula (2.6) are known in the art, are commercially available or can be prepared by methods known in the art, such as J. Med Chem. (1985) 28, 1447; Org. Synth. Coll. Vol III, (1955), p172; and Eur. J. Med. Chem. (1994) 29, p. 33, or by methods disclosed hereinafter, such as in Schemes IV and V. Similarly, carbadiimide coupling agents such as DEC and DCC are well known and commercially available. The tricylic compounds used as starting materials, such as compound (11.0), inorganic and organic bases, and alcohols can be prepared using known methods in the art, such as taught in See J. K. Wong et al., Bioorganic & Medicinal Chemistry Letters, Vol. 3, No. 6, pp. 1073–1078, (1993); U.S. Pat. Nos. 5,089,496; 5,151,423; 4,454,143; 4,355,036; PCT/US94/11390 (WO95/10514); PCT/US94/11391 (WO 95/10515); PCT/US94/11392 (WO95/10516); Stanley R. Sandler and Wolf Karo, Organic Functional Group Preparations, 2nd Edition, Academic Press, Inc., San Diego, Calif., Vol. 1–3, (1983), and in J. March, Advanced Organic Chemistry, Reactions & Mechanisms, and Structure, 3rd Edition, John Wiley & Sons, New York, 1346 pp. (1985). Alternative mechanistic pathways and analogous structures within the scope of the invention may be apparent to those skilled in the art.

Starting materials used to prepare the compounds of the present invention are depicted in Scheme IV:

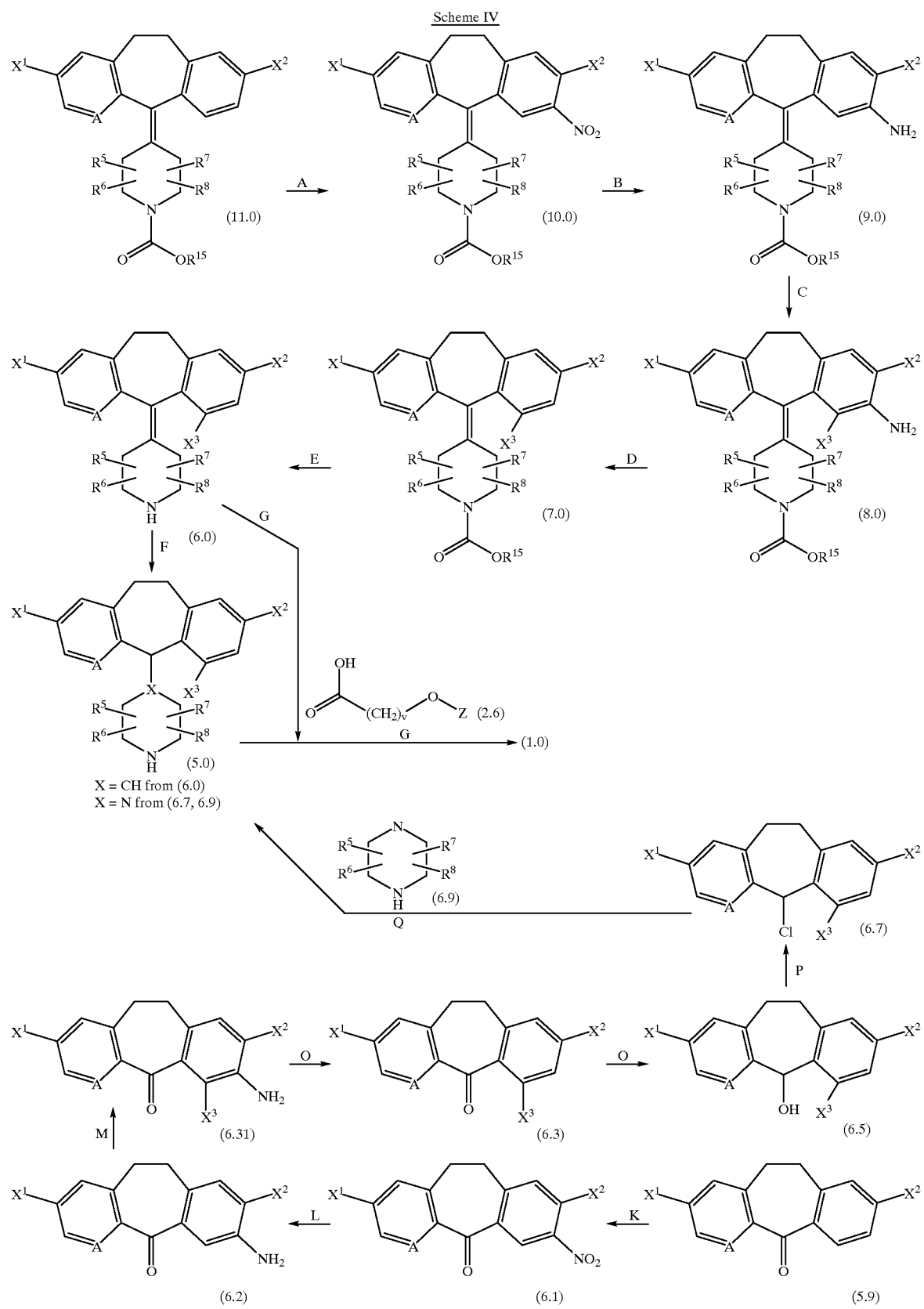
Scheme IV wherein for Scheme IV,

A, X, $X^1$, $X^2$, $X^3$, Z, $R^5$, $R^6$, $R^7$ and $R^8$, v and the solid and dotted lines are as defined hereinbefore; and $R^{15}$ can represent any of the values for $R^{10}$ and $R^{12}$ as defined hereinbefore.

In Step A (Scheme IV), compounds of formula (10.0) can be prepared by reacting the compounds of formula (11.0) with a nitrating agent and/or optional protic or aprotic solvent such as those described hereinbefore. In a first procedure, compound (11.0) is reacted with about an equimolar amount of a nitrate salt, such as potassium nitrate, and acid, such as sulfuric acid at temperatures ranging from about −20° to +5° C. In a second procedure, compound (11.0) is reacted with about an equimolar amount of nitric acid and acid, such as sulfuric acid at temperatures ranging from about −20° to +5° C. In a third procedure, compound (11.0) is treated with a mixture comprised of about two equivalents of trifluoromethanesulfonic acid and about one equivalent nitric acid in a solvent such as trifluoromethanesulfonic acid. In a fourth procedure, compound (11.0) is treated with a mixture comprised of about one equivalent of fuming nitric acid and about ten equivalents of trifluoromethanesulfonic anhydride in a solvent such as nitromethane. In a fifth procedure, compound (11.0) is treated with a nitronium salt, such as nitronium tetrafluoroborate, in a solvent, such as sulfolane. In a sixth procedure, compound (11.0) is reacted with fuming nitric acid at temperatures ranging from about −20° to +50° C.

In Step B (Scheme IV), compounds of formula (9.0) can be prepared by reacting compounds of the formula (10.0) with a reducing agent. In a first procedure, compound (10.0) can be reacted with about ten equivalents of a metal, such as iron, in a solvent, such as ethanol, in the presence of a salt, such as calcium chloride, at temperatures ranging from about 0° to +80° C. In a second procedure, compound (10.0) can be reacted with about ten equivalents of a metal, such as zinc, in a solvent, such as ethanol, in the presence of an acid, such as acetic acid at temperatures ranging from about 0° to +80° C. In a third procedure, compound (10.0) can be reacted with about five equivalents of stannous chloride hydrate in a solvent, such as ethyl acetate. In a fourth procedure, compound (10.0) can be reacted with about ten equivalents of a metal, such as tin, in a solvent, such as ethanol, in the presence of an acid, such as hydrochloric acid.

In Step C (Scheme IV), compounds of formula (8.0) can be prepared by reacting compounds of the formula (9.0) with a halogenating agent. In a first procedure, compound (9.0) can be reacted with an excess of an elemental halogen, such as bromine, in a suitable solvent, such as acetic acid at temperatures ranging from about 0° to +80° C. In a second procedure, compound (9.0) can be reacted with an excess of a mineral acid, such as hydrogen bromide, in a suitable solvent, such as dimethyl sulfoxide at temperatures ranging from about 20° C. to about 135° C. In a third procedure, compound (9.0) can be reacted with a salt, such as pyridinium bromide perbromide, in a solvent, such as THF, at temperatures from about 0° to +40° C. In a fourth procedure, compound (9.0) can be reacted with a halogen, such as chlorine, in the presence of a Lewis acid, such as iron(III) chloride, in a suitable solvent, such as dichloromethane.

In Step D (Scheme IV), compounds of formula (7.0) can be prepared by reacting compounds of the formula (8.0) with an oxidizing agent followed by a reducing agent, or by reacting compounds of the formula (8.0) with an oxidizing agent in the presence of a hydrogen atom source. In a first procedure, compound (8.0) can be reacted with a diazotizing agent, such as t-butyl nitrite, in a solvent and hydrogen atom source, such as DMF at temperatures from about 0° to +100° C. In a second procedure, compound (8.0) can be reacted with a diazotizing agent, such as sodium nitrite, and an acid, such as hydrochloric acid, and a reducing agent, such as hypophosphorous acid at temperatures from about −15° to +50° C. In a third procedure, compound (8.0) can be reacted with a diazotizing agent, such as sodium nitrite, and an acid, such as aqueous sulfuric acid, followed by treatment with a metal, such as copper. In a fourth procedure, compound (8.0) can be reacted with a diazotizing agent, such as sodium nitrite, and an acid, such as fluoboric acid, followed by treatment with a reducing agent, such as sodium borohydride.

In Step E (Scheme IV), compounds of formula (6.0) can be prepared by reacting compounds of the formula (7.0) under hydrolysis conditions. In a first procedure, compound (7.0) can be reacted with an acid, such as hydrochloric acid, at temperatures from about 20° to +90° C. In a second procedure, compound (7.0) can be reacted with a base, such as aqueous sodium hydroxide, in a suitable solvent, such as ethanol, at temperatures from about 20° to +90° C. In a third procedure, compound (7.0) can be reacted with a nucleophile, such as hydrazine hydrate, in a solvent, such as ethanol, with an optional base, such as sodium hydroxide, at temperatures from about 20° to +90° C. In a fourth procedure, compound (7.0) can be reacted with a silyl chloride, such as trimethylsilyl chloride, in a solvent, such as THF or $CH_2Cl_2$ at temperatures ranging from about 0° C. to reflux. In a fifth procedure, compound (7.0) can be reacted with an acid, such as trifluoroacetic acid, in an aprotic solvent, such as $CH_2Cl_2$.

In Step F (Scheme IV), compounds of formula (5.0) wherein X =CH can be prepared by reacting compounds of the formula (6.0) under reducing conditions. Compound (6.0) can be reacted with an alkyl-metal hydride, such as diisobutyl aluminum hydride, in a solvent, such as toluene, at temperatures from about 0° to +90° C.

In Step G (Scheme IV), compounds of formula (1.0) can be prepared using the methods as described in Scheme I, hereinbefore.

In Step K (Scheme IV), compounds of formula (6.1) can be prepared by reacting the compound of formula (5.9) with a nitrating agent and/or optional protic or aprotic solvent according to the procedures described in Step A (Scheme IV).

In Step L (Scheme IV), compounds of formula (6.2) can be prepared by reacting the compound of formula (6.1) with a reducing agent according to the procedures described in Step B (Scheme IV).

In Step M (Scheme IV), compounds of formula (6.31) can be prepared by reacting the compound of formula (6.2) with a halogenating agent according to the procedures described in Step C (Scheme IV).

In Step N (Scheme IV), compounds of formula (6.3) can be prepared by reacting the compound of formula (6.31) with an oxidizing agent followed by a reducing agent, or by reacting compounds of the formula (6.31) with an oxidizing agent in the presence of a hydrogen atom source according to the procedures described in Step D (Scheme IV).

In Step O (Scheme IV), compounds of formula (6.5) can be prepared by reacting compounds of formula (6.3) with sodium borohyciride ($NaBH_4$) in a solvent such as ethanol/toluene under reflux conditions for 10 minutes or at 25° C. for two hours or more.

In Step P (Scheme IV), compounds of formula (6.7) can be prepared by reacting compounds of formula (6.5) with SOCl$_2$ in a solvent such as CH$_2$Cl$_2$ at a temperature of about 25° C. for about 4 hours or more.

In Step Q (Scheme IV), compounds of formula (5.0) wherein X=N, can be prepared by reacting compounds (6.7) with an excess amount of the piperazine compound of formula (6.9) in a solvent such as THF at 25° C. or reflux for one hour or more.

Additional starting materials which can be used to prepare the compounds of the present invention are depicted in Scheme V.

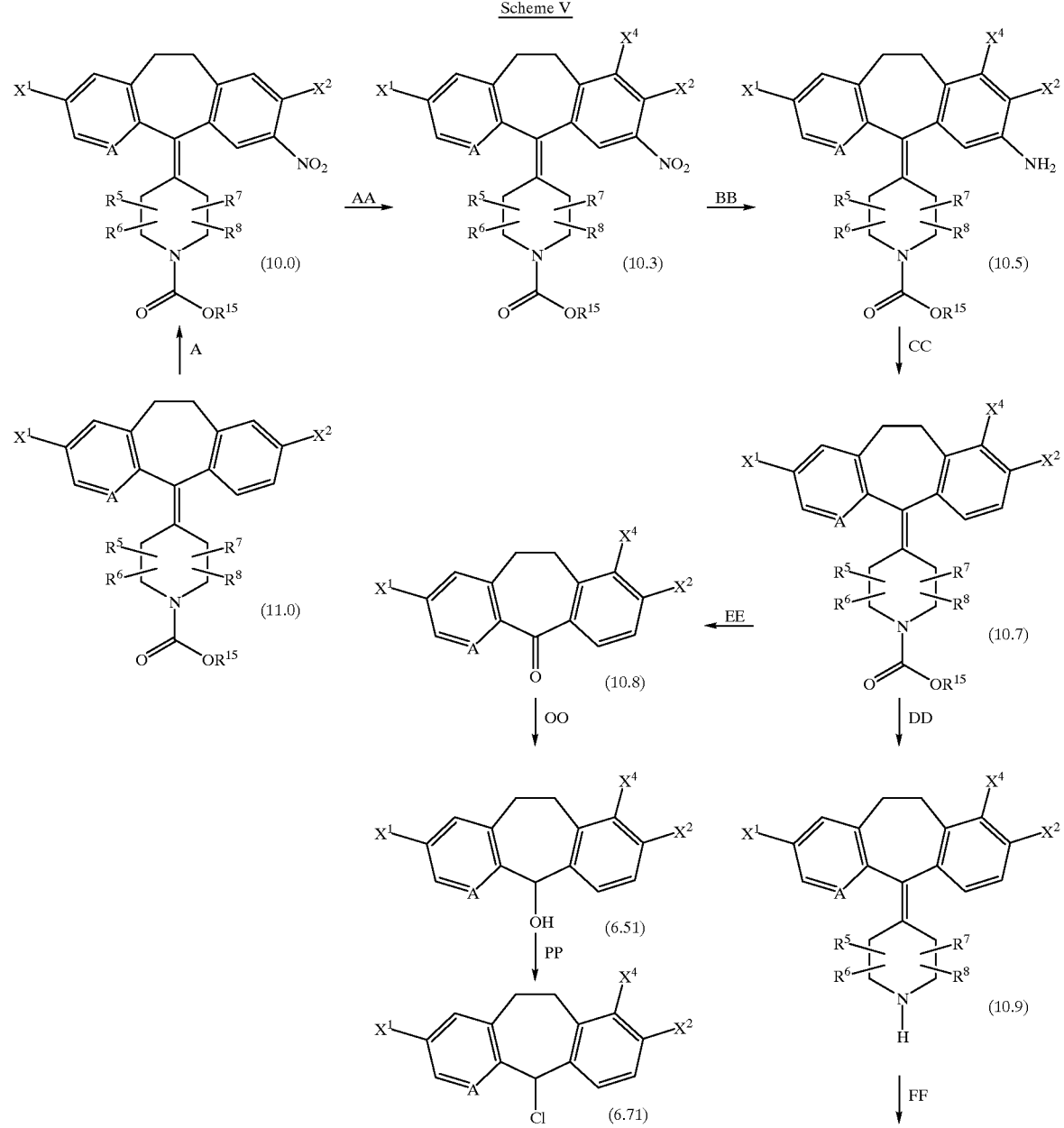

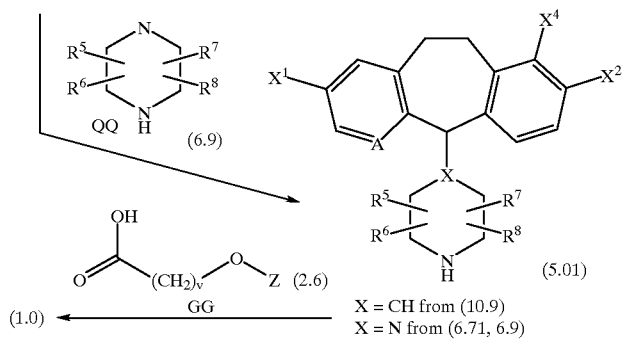

In Step A (Scheme V), compounds of fomula (10.0) can be prepared from compound of formula (11.0) using the procedures described in Scheme IV, Step A.

In Step AA(Scheme V), compounds of formula (10.3) can be prepared by reacting compound of formula (10.0) with 1,3-dibromo-5,5-dimethylhydantoin in an acid, such as tri-fluoromethane sulfonic acid or sulfuric acid for about 24 h or more at 25° C.

In Step BB (Scheme V), compounds of the formula (10.5) can be prepared by treating the compounds of formula (10.3) with a reducing agent, using the procedures taught in Scheme IV, Step B.

In Step CC (Scheme V), compounds of formula (10.7) can be prepared by reacting compounds of formula (10.5) with sodium nitrite ($NaNO_2$) in concentrated aqueous HCl at temperatures ranging from about −10° C. to 0° C. for about 2 h or more, then treating the reaction mixture with phosphorous acid ($H_3PO_2$) at 0° C. for 4 h or more.

In Step DD(Scheme V), compounds of formula (10.9) can be prepared by reacting compounds of formula (10.7) with concentrated aqueous HCl at about 85° C. for about 18 h or more. Compound (10.9) can be reacted using the same procedures described in Scheme IV for treating compound (5.0) and (6.0) and subsequent intermediates therefrom, in order to obtain the desired compounds of formula (1.0).

In Step EE (Scheme V), compounds of formula (10.8) can be prepared by reacting compound of formula (10.7) with $NaIO_4$ and $RuO_2$ in acetonitrile and water for about 18 to 24 h or more at 25° C.

In Step FF(Scheme V), compounds of formula (5.01) wherein X=CH can be prepared by reacting compounds of the formula (10.9) under reducing conditions. Compound (10.9) can be reacted with an alkyl-metal hydride, such as diisobutyl aluminum hydride, in a solvent, such as toluene, at temperatures from about 0° to +90° C.

In Step GG(Scheme V), compounds of formula (1.0) can be prepared using the methods as described in Scheme I, hereinbefore.

In Step OO(Scheme V), compounds of formula (6.51) can be prepared by reacting compounds of formula (10.8) with sodium borohydride ($NaBH_4$) in a solvent such as ethanol/toluene under reflux conditions for 10 minutes or at 25° C. for two hours or more.

In Step PP (Scheme V), compounds of formula (6.71) can be prepared by reacting compounds of formula (6.51) with $SOCl_2$ in a solvent such as $CH_2Cl_2$ at a temperature of about 25° C. for about 4 hours or more.

In Step QQ (Scheme V), compounds of formula (5.01) wherein X=N, can be prepared by reacting compounds (6.71) with an excess amount of the piperazine compound of formula (6.9) in a solvent such as THF at 25° C. or reflux for one hour or more.

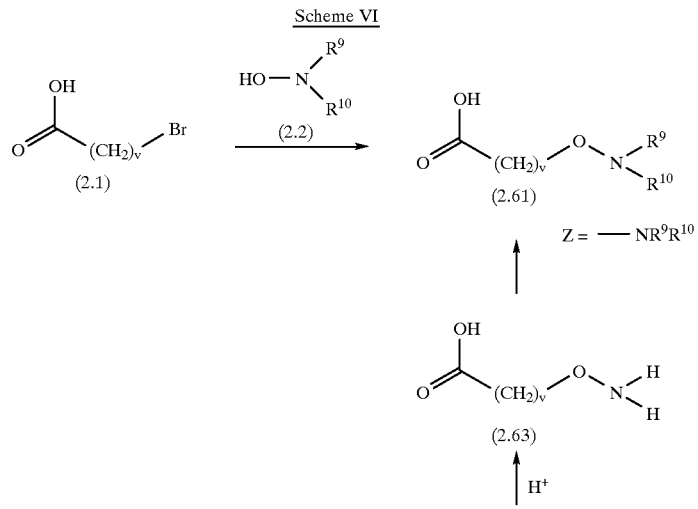

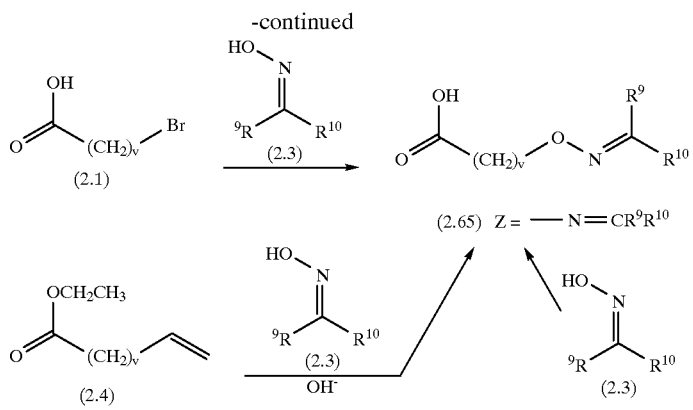

wherein v, $R^9$ and $R^{10}$ are defined hereinbefore.

In Scheme VI, aminooxy carboxylic acids of formula (2.61) wherein $Z=-NR^9R^{10}$ can be prepared by reacting a compound of formula (2.1) with an amino alcohol of formula (2.2) in a protic or aprotic solvent such as water or DMF with a base such as sodium hydroxide or sodium carbonate at a temperature of 25° to 100° C. Alternatively, aminooxy carboxylic acids of formula (2.61) can be prepared by reacting a compound of formula (2.63) with the appropriate reagent containing the requisite $R^9$ and $R^{10}$ groups to give the desired $R^9$ and $R^{10}$ substituents. For example, alkyl substituents can be obtained using alkylating reagents such as an alkyl halide; acyl substituents can be obtained using acylating reagents such as an acyl halide; sulfonyl substituents can be obtained using sulfonating reagents such as sulfonyl halide.

In Scheme VI, compound (2.63) can be prepared by hydrolyzing the oxime compound of formula (2.65) with an inorganic acid, such as hydrochloric, sulfuric, phosphoric and the like, or an organic acid such as acetic acid, at temperatures of 25° to 100° C.

In Scheme VI, the oxime compound of formula (2.65) wherein $Z=-N=CR^9R^{10}$ can be prepared by reacting the brominated carboxy compound of formula (2.1) with oxime compound (2.3) in a protic or aprotic solvent such as DMF, benzene or water in the presence of a base such as sodium hydroxide or sodium carbonate at a temperature ranging from 0° to 100° C. Alternatively, oxime compound (2.65) can be prepared by reacting vinyl compound of formula (2.4) with oxime compound (2.3) in a alcoholic solvent such as ethanol, at a temperature of 0° to 100° C., followed by treatment with base (OH⁻) such as sodium or potassium hydroxide, at temperatures of 0° to 100° C. Alternatively, oxime compound (2.65) can be prepared by treating compound (2.63) with pyridine or alcoholic solvents such as ethanol using equimolar amounts of the corresponding aldehyde or ketone reagents.

The following preparative examples are intended to exemplify selected starting materials for preparing compounds of the present invention.

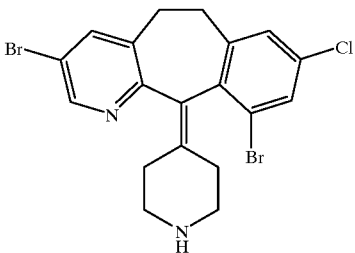

PREPARATIVE EXAMPLE 1

Step A:

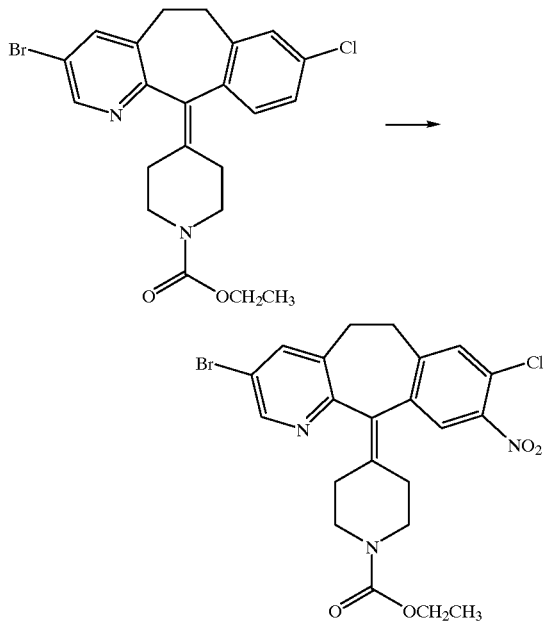

Combine 15 g (38.5 mmol) of 4-(8-chloro-3-bromo-5,6-dihydro-11H-benzo[5,6]cyclohepta[1,2-b]pyridin-11-ylidene)-1-piperidine-1-carboxylic acid ethyl ester (as taught in Preparative Example 47 of PCT/US94/11392) and 150 mL of concentrated $H_2SO_4$ at −5° C., then add 3.89 g (38.5 mmol) of $KNO_3$ and stir for 4 hours. Pour the mixture into 3 L of ice and basify with 50% NaOH (aqueous). Extract with $CH_2Cl_2$, dry over $MgSO_4$, then filter and concentrate in vacuo to a residue. Recrystallize the residue from acetone to give 6.69 g of the product.

Step B:

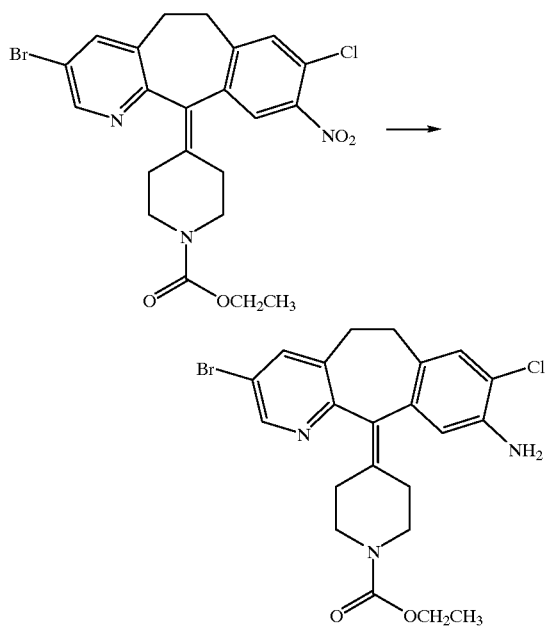

Combine 6.69 g (13.1 mmol) of the product of Step A and 100 mL of 85% EtOH/water, then add 0.66 g (5.9 mmol) of CaCl$_2$ and 6.56 g (117.9 mmol) of Fe and heat the mixture at reflux overnight. Filter the hot reaction mixture through Celite® and rinse the filter cake with hot EtOH. Concentrate the filtrate in vacuo to give 7.72 g of the product.

Step C:

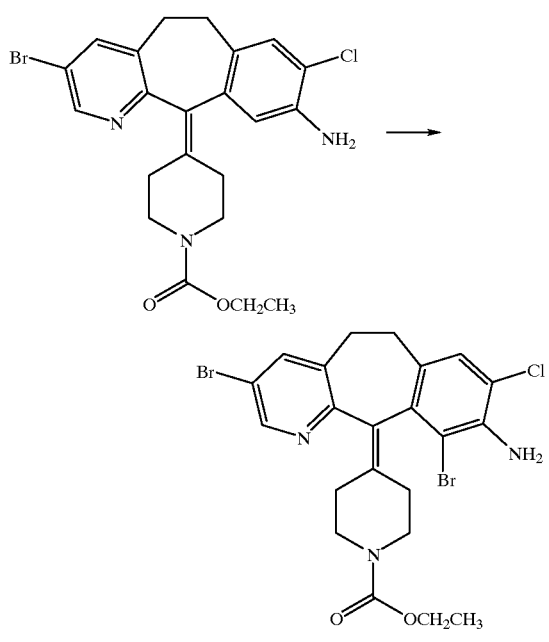

Combine 7.70 g of the product of Step B and 35 mL of HOAc, then add 45 mL of a solution of Br$_2$ in HOAc and stir the mixture at room temperature overnight. Add 300 mL of 1 N NaOH (aqueous), then 75 mL of 50% NaOH (aqueous) and extract with EtOAc. Dry the extract over MgSO$_4$ and concentrate in vacuo to a residue. Chromatograph the residue (silica gel, 20%–30% EtOAc/hexane) to give 3.47 g of the product (along with another 1.28 g of partially purified product).

Step D:

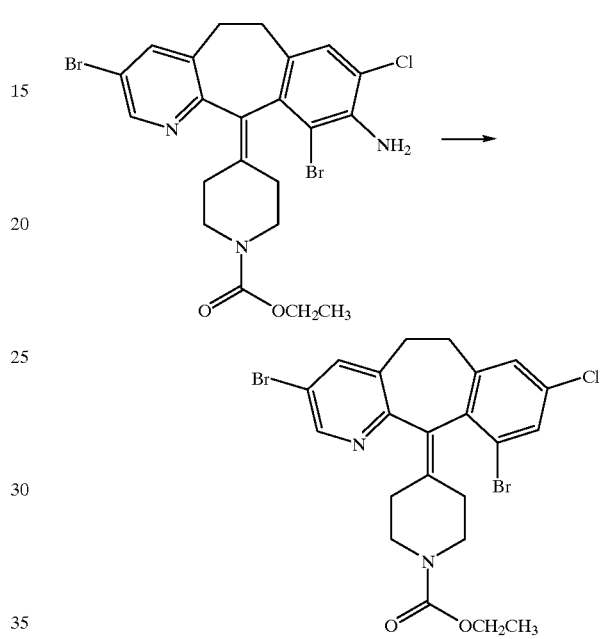

Combine 0.557 g (5.4 mmol) of t-butylnitrite and 3 mL of DMF, and heat the mixture at to 60°–70° C. Slowly add (dropwise) a mixture of 2.00 g (3.6 mmol) of the product of Step C and 4 mL of DMF, then cool the mixture to room temperature. Add another 0.64 mL of t-butylnitrite at 40° C. and reheat the mixture to 60°–70° C. for 0.5 hrs. Cool to room temperature and pour the mixture into 150 mL of water. Extract with CH$_2$Cl$_2$, dry the extract over MgSO$_4$ and concentrate in vacuo to a residue. Chromatograph the residue (silica gel, 10%–20% EtOAc/hexane) to give 0.74 g of the product.

Step E:

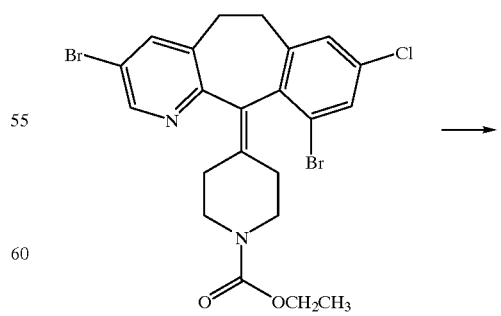

31
-continued

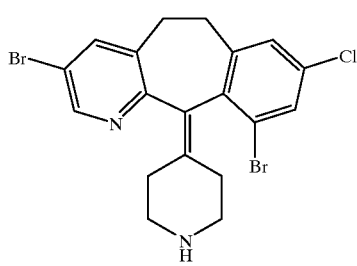

Combine 0.70 g (1.4 mmol) of the product of Step D and 8 mL of concentrated HCl (aqueous) and heat the mixture at reflux overnight. Add 30 mL of 1 N NaOH (aqueous), then 5 mL of 50% NaOH (aqueous) and extract with CH₂Cl₂. Dry the extract over MgSO₄ and concentrate in vacuo to give 0.59 g of the title compound.

PREPARATIVE EXAMPLE 2

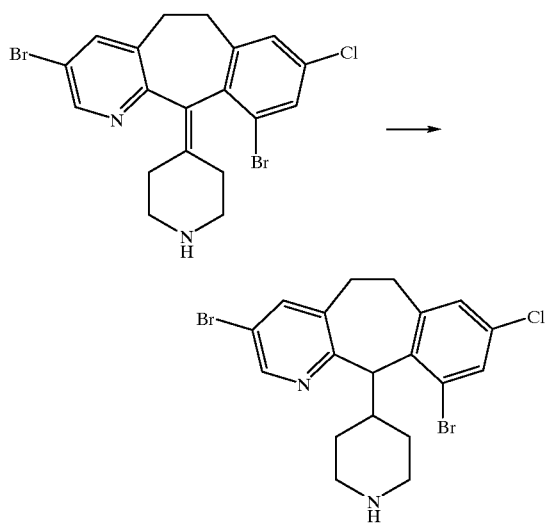

[racemic as well as (+)- and (−)-isomers]

Prepare a solution of 8.1 g of the title compound from Preparative Example 7 in toluene and add 17.3 mL of a 1M solution of DIBAL (diisobutyl aluminum hydride) in toluene. Heat the mixture at reflux and slowly add (dropwise) another 21 mL of 1M DIBAL/toluene solution over a period of 40 min. Cool the reaction mixture to about 0° C. and add 700 mL of 1 M HCl (aqueous). Separate and discard the organic phase. Wash the aqueous phase with CH₂Cl₂, discard the extract, then basify the aqueous phase by adding 50% NaOH (aqueous). Extract with CH₂Cl₂, dry the extract over MgSO₄ and concentrate in vacuo to give 7.30 g of the title compound, which is a racemic mixture of enantiomers.

32
PREPARATIVE EXAMPLE 3—PREPARATION OF ENANTIOMERS

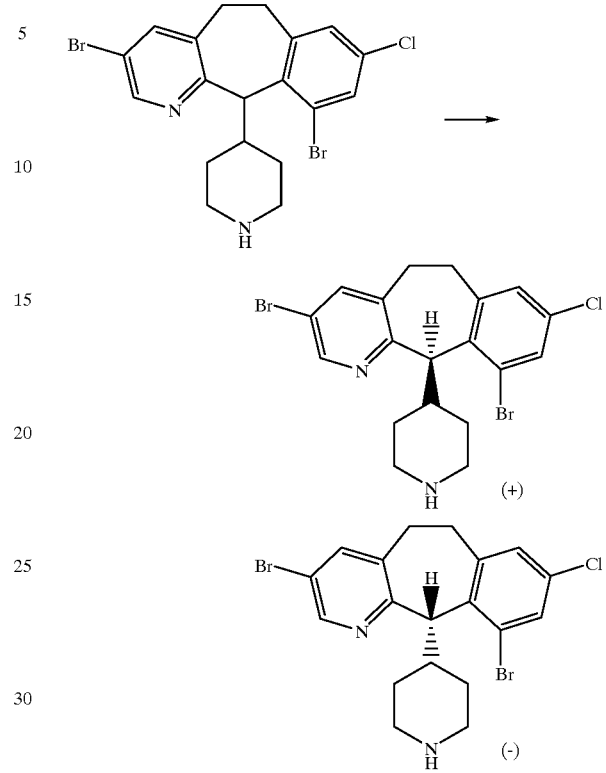

The racemic title compound of Preparative Example 1 is separated by preparative chiral chromatography (Chiralpack AD, 5 cm×50 cm column, using 20% iPrOH/hexane+0.2% diethylamine), to give the (+)-isomer and the (−)-isomer of the title compound. Alternatively, the enantiomers can also be separated by crystallization with an amino acid such as N-acetylphenylalanine.

PREPARATIVE EXAMPLE 6

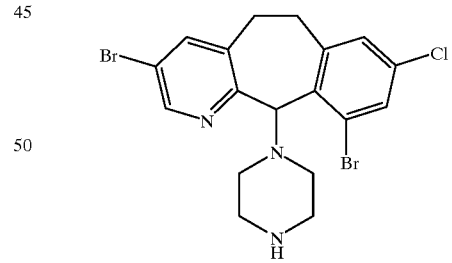

[racemic as well as (+)- and (−)-enantiomer]

Step A:

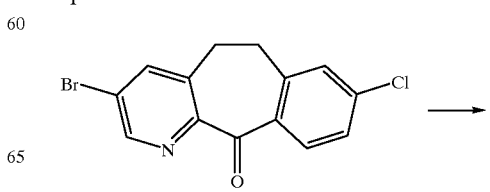

-continued

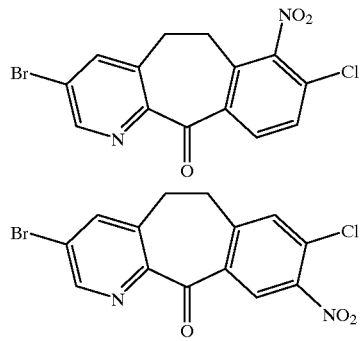

Combine 40.0 g (0.124 mole) of the starting ketone (as taught in Preparative Example 20 of PCT/US 94/11392) and 200 mL of H$_2$SO$_4$ and cool to 0° C. Slowly add 13.78 g (0.136 mole) of KNO$_3$ over a period of 1.5 hrs., then warm to room temperature and stir overnight. Work up the reaction using substantially the same procedure as described for Preparative Example 4, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds. MH$^+$ (9-nitro)=367.

Step B:

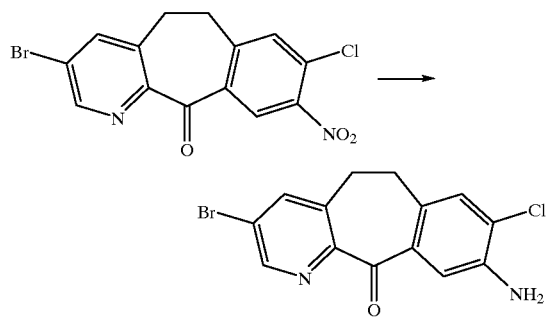

React 28 g (76.2 mmol) of the 9-nitro product of Step A, 400 mL of 85% EtOH/water, 3.8 g (34.3 mmol) of CaCl$_2$ and 38.28 g (0.685 mole) of Fe at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of CH$_2$Cl$_2$, wash with 300 mL of water and dry over MgSO$_4$. Filter and concentrate in vacuo to a residue, then chromatograph (silica gel, 30% EtOAc/CH$_2$Cl$_2$) to give 24 g of the product.

Step C:

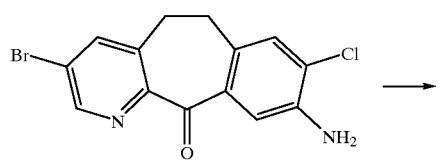

-continued

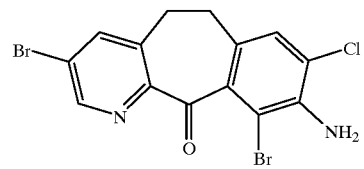

Combine 13 g (38.5 mmol) of the product of Step B, 140 mL of HOAc and slowly add a solution of 2.95 mL (57.8 mmol) of Br$_2$ in 10 mL of HOAc over a period of 20 min. Stir the reaction mixture at room temperature, then concentrate in vacuo to a residue. Add CH$_2$Cl$_2$ and water, then adjust to pH=8–9 with 50% NaOH (aqueous). Wash the organic phase with water, then brine and dry over Na$_2$SO$_4$. Concentrate in vacuo to give 11.3 g of the product.

Step D:

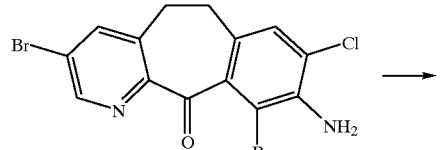

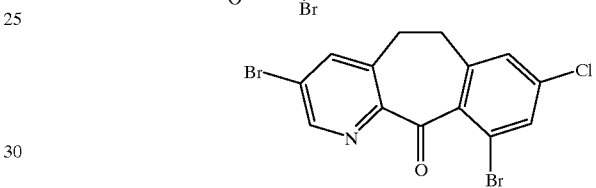

Cool 100 mL of concentrated HCl (aqueous) to 0° C., then add 5.61 g (81.4 mmol) of NaNO$_2$ and stir for 10 min. Slowly add (in portions) 11.3 g (27.1 mmol) of the product of Step C and stir the mixture at 0°–3° C. for 2.25 hrs. Slowly add (dropwise) 180 mL of 50% H$_3$PO$_2$ (aqueous) and allow the mixture to stand at 0° C. overnight. Slowly add (dropwise) 150 mL of 50% NaOH over 30 min., to adjust to pH=9, then extract with CH$_2$Cl$_2$. Wash the extract with water, then brine and dry over Na$_2$SO$_4$. Concentrate in vacuo to a residue and chromatograph (silica gel, 2% EtOAc/CH$_2$Cl$_2$) to give 8.6 g of the product.

Step E:

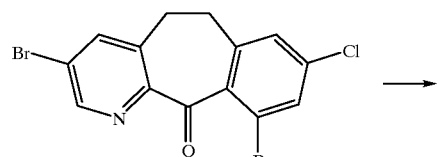

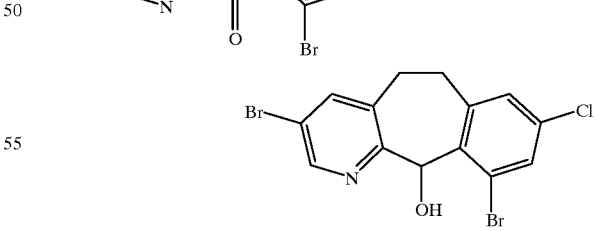

Combine 8.6 g (21.4 mmol) of the product of Step D and 300 mL of MeOH and cool to 0°–2° C. Add 1.21 g (32.1 mmol) of NaBH$_4$ and stir the mixture at ~0° C. for 1 hr. Add another 0.121 g (3.21 mmol) of NaBH$_4$, stir for 2 hr. at 0° C., then let stand overnight at 0° C. Concentrate in vacuo to a residue then partition the residue between CH$_2$Cl$_2$ and water. Separate the organic phase and concentrate in vacuo (50° C.) to give 8.2 g of the product.

Step F:

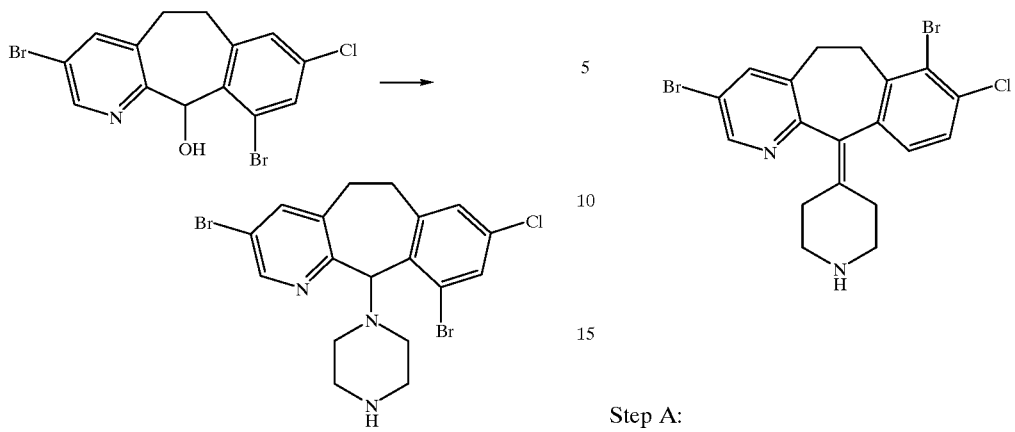

Combine 8.2 g (20.3 mmol) of the product of Step E and 160 mL of $CH_2Cl_2$, cool to 0° C., then slowly add (dropwise) 14.8 mL (203 mmol) of $SOCl_2$ over a 30 min. period. Warm the mixture to room temperature and stir for 4.5 hrs., then concentrate in vacuo to a residue, add $CH_2Cl_2$ and wash with 1 N NaOH (aqueous) then brine and dry over $Na_2SO_4$. Concentrate in vacuo to a residue, then add dry THF and 8.7 g (101 mmol) of piperazine and stir at room temperature overnight. Concentrate in vacuo to a residue, add $CH_2Cl_2$, and wash with 0.25 N NaOH (aqueous), water, then brine. Dry over $Na_2SO_4$ and concentrate in vacuo to give 9.46 g of the crude product. Chromatograph (silica gel, 5% MeOH/$CH_2Cl_2$+$NH_3$) to give 3.59 g of the title compound, as a racemate.

Step G—Separation of Enantiomers:

PREPARATIVE EXAMPLE 7

Step A:

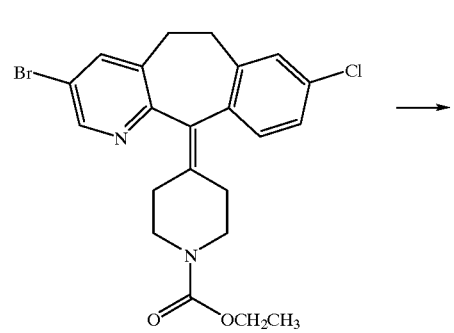

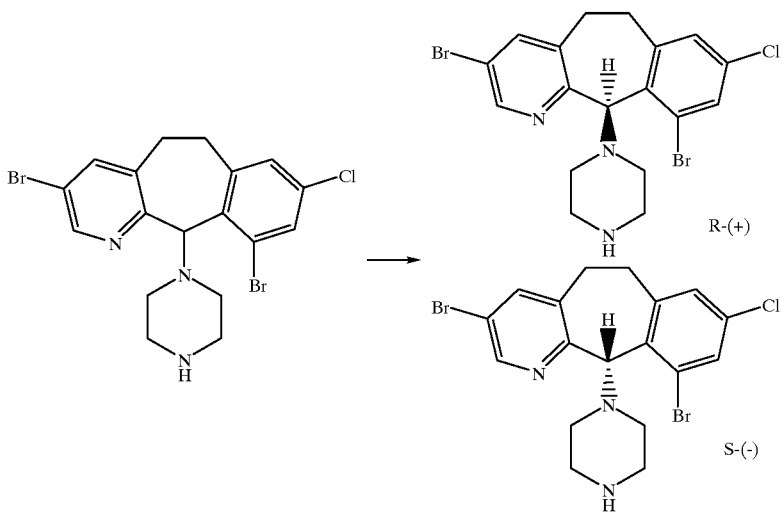

The racemic title compound from Step F (5.7 g) is chromatographed by preparative chiral chromatography (Chiralpack AD, 5 cm×50 cm column, flow rate 100 mL/min) using 30% iPrOH/hexane+0.2% diethylamine, to give 2.88 g of the R-(+)-enantiomer and 2.77 g of the S-(−)-enantiomer of the title compound.

-continued

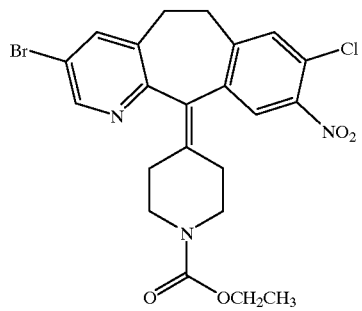

Combine 25.86 g (55.9 mmol) of 4-(8-chloro-3-bromo-5,6-dihydro-11H-benzo[5,6]cyclohepta[1,2-b]pyridin-11-ylidene)-1-piperidinie-1-carboxylic acid ethyl ester and 250 mL of concentrated $H_2SO_4$ at −5° C., then add 4.8 g (56.4 mmol) of $NaNO_3$ and stir for 2 hours. Pour the mixture into 600 g of ice and basify with concentrated $NH_4OH$ (aqueous). Filter the mixture, wash with 300 mL of water, then extract with 500 mL of $CH_2Cl_2$. Wash the extract with 200 mL of water, dry over $MgSO_4$, then filter and concentrate in vacuo to a residue. Chromatograph the residue (silica gel, 10% $EtOAc/CH_2Cl_2$) to give 24.4 g (86% yield) of the product. m.p.=165–167° C.

Step B:

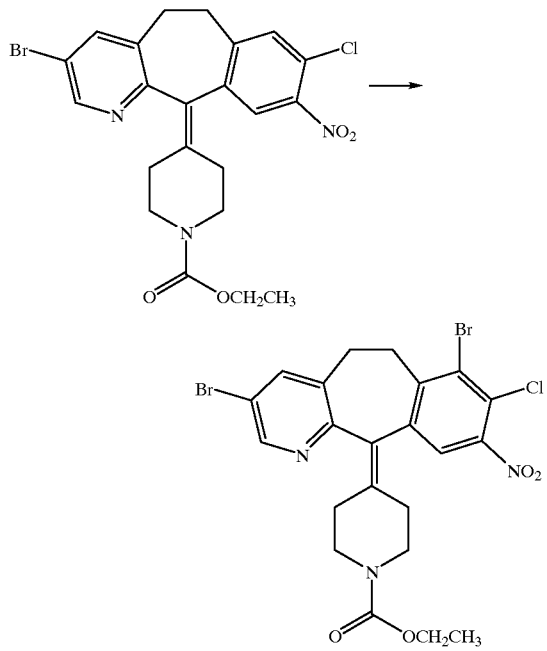

Combine 20 g (40.5 mmol) of the product of Step A and 200 mL of concentrated $H_2SO_4$ at 20° C., then cool the mixture to 0° C. Add 7.12 g (24.89 mmol) of 1,3-dibromo-5,5-dimethyl-hydantoin to the mixture and stir for 3 hours at 20° C. Cool to 0° C., add an additional 1.0 g (3.5 mmol) of the dibromohydantoin and stir at 20° C. for 2 hours. Pour the mixture into 400 g of ice, basify with concentrated $NH_4OH$ (aqueous) at 0° C., and collect the resulting solid by filtration. Wash the solid with 300 mL of water, slurry in 200 mL of acetone and filter to provide 19.79 g (85.6% yield) of the product.

Step C:

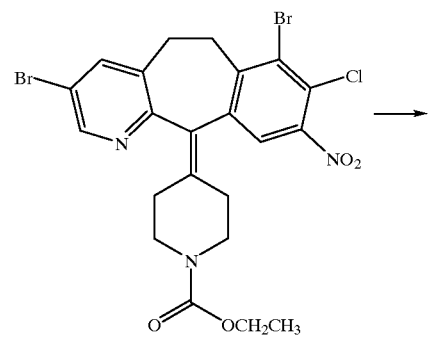

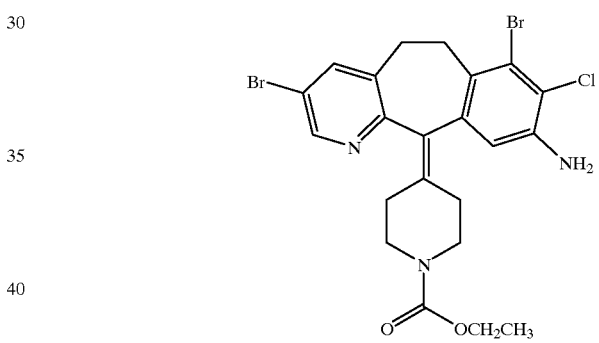

Combine 25 g (447 mmol) of Fe filings, 10 g (90 mmol) of $CaCl_2$ and a suspension of 20 g (34.19 mmol) of the product of Step B in 700 mL of 90:10 EtOH/water at 50° C. Heat the mixture at reflux overnight, filter through Celite® and wash the filter cake with 2×200 mL of hot EtOH. Combine the filtrate and washes, and concentrate in vacuo to a residue. Extract the residue with 600 mL of $CH_2Cl_2$, wash with 300 mL of water and dry over $MgSO_4$. Filter and concentrate in vacuo to a residue, then chromatograph (silica gel, 30% $EtOAc/CH_2Cl_2$) to give 11.4 g (60% yield) of the product.

Step D:

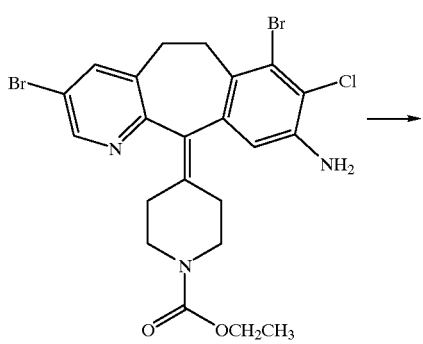

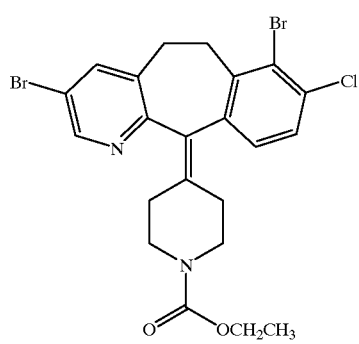

Slowly add (in portions) 20 g (35.9 mmol) of the product of Step C to a solution of 8 g (116 mmol) of NaNO₂ in 120 mL of concentrated HCl (aqueous) at −10° C. Stir the resulting mixture at 0° C. for 2 hours, then slowly acid (dropwise) 150 mL (1.44 mole) of 50% H₃PO₂ at 0° C. over a 1 hour period. Stir at 0° C. for 3 hours, then pour into 600 g of ice and basify with concentrated NH₄OH (aqueous). Extract with 2×300 mL of CH₂Cl₂, dry the extracts over MgSO₄, then filter and concentrate in vacuo to a residue. Chromatograph the residue (silica gel, 25% EtOAc/hexanes) to give 13.67 g (70% yield) of the product.

Step E:

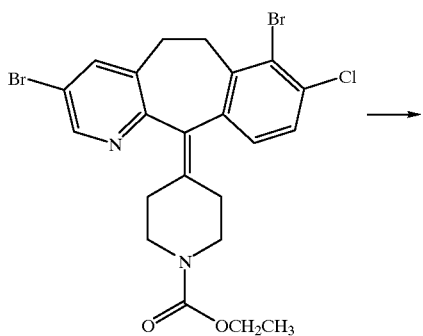

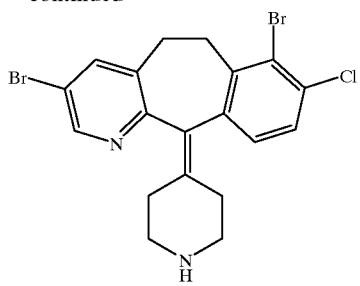

Combine 6.8 g (12.59 mmol) of the product of Step D and 100 mL of concentrated HCl (aqueous) and stir at 85° C. overnight. Cool the mixture, pour it into 300 g of ice and basify with concentrated NH₄OH (aqueous). Extract with 2×300 mL of CH₂Cl₂, then dry the extracts over MgSO₄. Filter, concentrate in vacuo to a residue, then chromatograph (silica gel, 10% MeOH/EtOAc+2% NH₄OH (aqueous)) to give 5.4 g (92% yield) of the title compound.

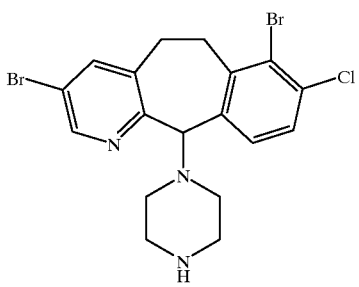

PREPARATIVE EXAMPLE 8

[racemic as well as (+)- and (−)-enantiomers]

Step A:

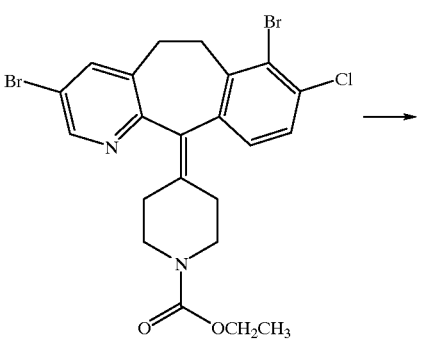

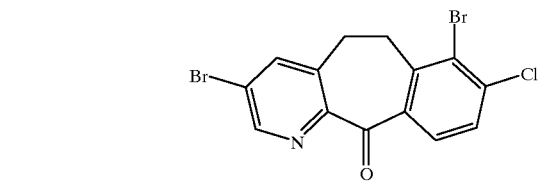

Combine 16.6 g (0.03 mole) of the product of Preparative Example 7, Step D, with a 3:1 solution of $CH_3CN$ and water (212.65 mL $CH_3N$ and 70.8 mL of water) and stir the resulting slurry overnight at room temperature. Add 32.833 g (0.153 mole) of $NaIO_4$ and then 0.31 g (2.30 mmol) of $RuO_2$ and stir at room temperature (the addition of $RuO_2$ is accompanied by an exothermic reaction and the temperature climbs from 20° to 30° C.). Stir the mixture for 1.3 hrs. (temperature returned to 25° C. after about 30 min.), then filter to remove the solids and wash the solids with $CH_2Cl_2$. Concentrate the filtrate in vacuo to a residue and dissolve the residue in $CH_2Cl_2$. Filter to remove insoluble solids and wash the solids with $CH_2Cl_2$. Wash the filtrate with water, concentrate to a volume of about 200 mL and wash with bleach, then with water. Extract with 6N HCl (aqueous). Cool the aqueous extract to 0° C. and slowly add 50% NaOH (aqueous) to adjust to pH=4 while keeping the temperature <30° C. Extract twice with $CH_2Cl_2$, dry over $MgSO_4$ and concentrate in vacuo to a residue. Slurry the residue in 20 mL of EtOH and cool to 0° C. Collect the resulting solids by filtration and dry the solids in vacuo to give 7.95 g of the product.

Step B:

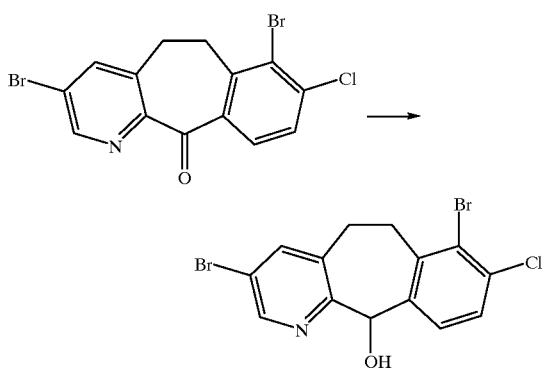

Combine 21.58 g (53.75 mmol) of the product of Step A and 500 mL of an anhydrous 1:1 mixture of EtOH and toluene, add 1.43 g (37.8 mmol) of $NaBH_4$ and heat the mixture at reflux for 10 min. Cool the mixture to 0° C., add 100 mL of water, then adjust to pH≈4–5 with 1M HCl (aqueous) while keeping the temperature <10° C. Add 250 mL of EtOAc and separate the layers. Wash the organic layer with brine (3×50 mL) then dry over $Na_2SO_4$. Concentrate in vacuo to a residue (24.01 g) and chromatograph the residue (silica gel, 30% hexane/$CH_2Cl_2$) to give the product. Impure fractions were purified by rechromatography. A total of 18.57 g of the product is obtained.

Step C:

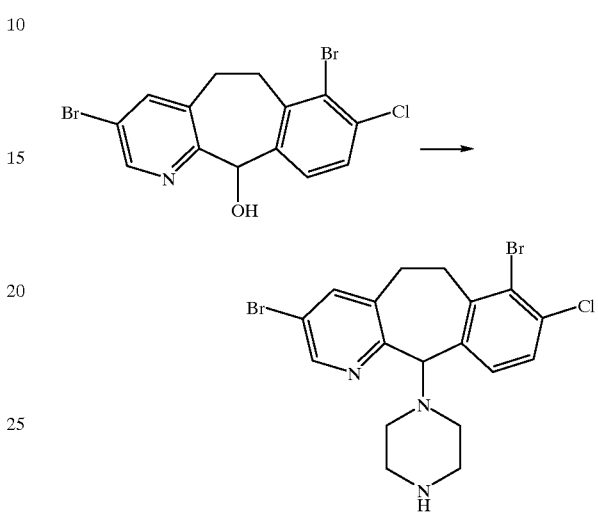

Combine 18.57 g (46.02 mmol) of the product of Step B and 500 mL of $CHCl_3$, then add 6.70 mL (91.2 mmol) of $SOCl_2$, and stir the mixture at room temperature for 4 hrs. Add a solution of 35.6 g (0.413 mole) of piperazine in 800 mL of THF over a period of 5 min. and stir the mixture for 1 hr. at room temperature. Heat the mixture at reflux overnight, then cool to room temperature and dilute the mixture with 1 L of $CH_2Cl_2$. Wash with water (5×200 mL), and extract the aqueous wash with $CHCl_3$ (3×100 mL). Combine all of the organic solutions, wash with brine (3×200 mL) and dry over $MgSO_4$. Concentrate in vacuo to a residue and chromatograph (silica gel, gradient of 5%, 7.5%, 10% MeOH/$CH_2Cl_2$+$NH_4OH$) to give 18.49 g of the title compound as a racemic mixture.

Step D—Separation of Enantiomers:

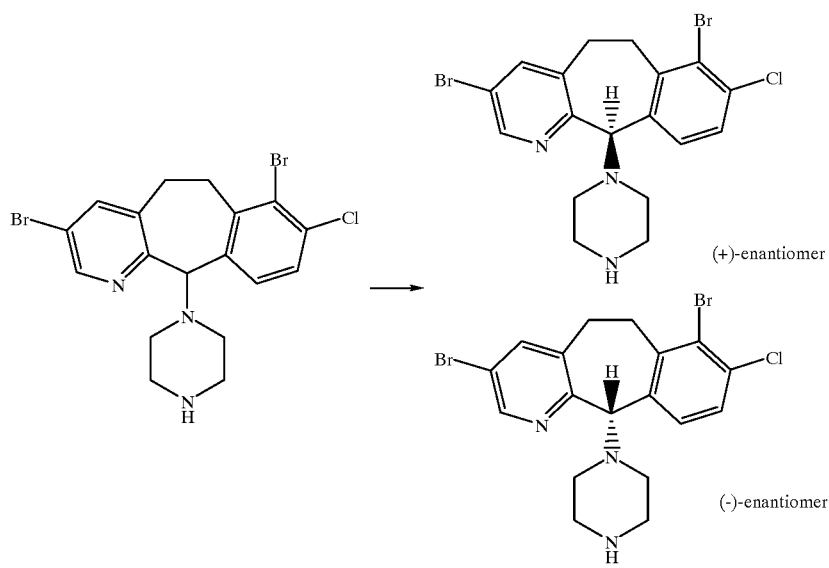

(+)-enantiomer (−)-enantiomer

The racemic title compound of Step C is separated by preparative chiral chromatography (Chiralpack AD, 5 cm×50 cm column, flow rate 100 mL/min., 20% iPrOH/hexane+0.2% diethylamine), to give 9.14 g of the (+)-enantiomer and 9.30 g of the (−)-enantiomer.

PREPARATIVE EXAMPLE 9

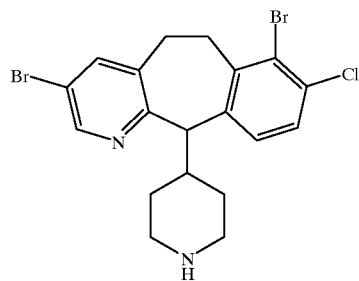

[racemic as well as (+)- and (−)-enantiomer]

Step A:

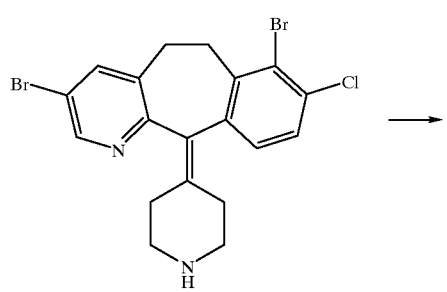

-continued

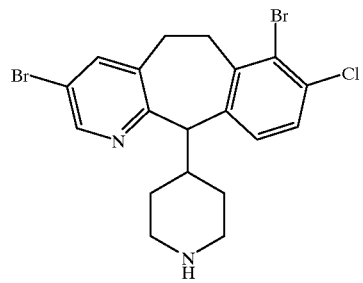

Combine 13 g (33.3 mmol) of the title compound from Preparative Example 7, and 300 mL of toluene at 20° C., then add 32.5 mL (32.5 mmol) of a 1M solution of DIBAL in toluene. Heat the mixture at reflux for 1 hr., cool to 20° C., add another 32.5 mL of 1M DIBAL solution and heat at reflux for 1 hr. Cool the mixture to 20° C. and pour it into a mixture of 400 g of ice, 500 mL of EtOAc and 300 mL of 10% NaOH (aqueous). Extract the aqueous layer with $CH_2Cl_2$ (3×200 mL), dry the organic layers over $MgSO_4$, then concentrate in vacuo to a residue. Chromatograph (silica gel, 12% $MeOH/CH_2Cl_2$+4% $NH_4OH$) to give 10.4 g of the title compound as a racemate.

Step B—Separation of Enantiomers:

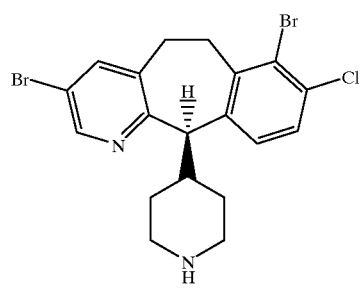

-continued

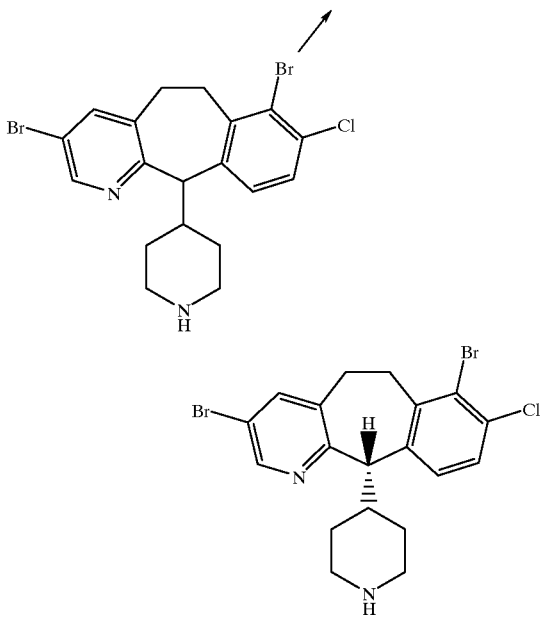

The racemic title compound of Step A is separated by preparative chiral chromatography (Chiralpack AD, 5 cm×50 cm column, using 5% iPrOH/hexane+0.2% diethylamine), to give the (+)-enantiomer and the (−)-enantiomer of the title compound.

PREPARATIVE EXAMPLE 10

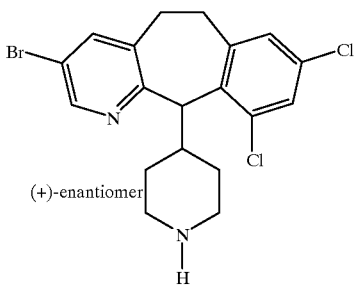
(+)-enantiomer

Step A:

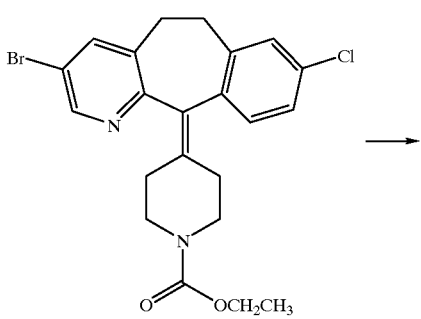

-continued

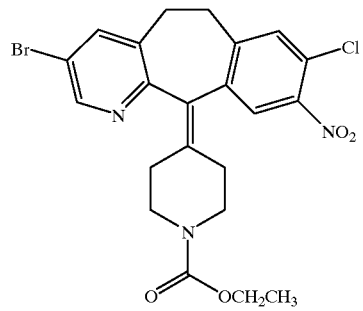

Combine 15 g (38.5 mmol) of 4-(8-chloro-3-bromo-5,6-dihydro-11H-benzo[5,6]cyciohepta[1,2-b]pyridin-11-ylidene)-1-piperidline-1-carboxylic acid ethyl ester and 150 mL of concentrated $H_2SO_4$ at −5° C., then add 3.89 g (38.5 mmol) of $KNO_3$ and stir for 4 hours. Pour the mixture into 3 L of ice and basify with 50% NaOH (aqueous). Extract with $CH_2Cl_2$, dry over $MgSO_4$, then filter and concentrate in vacuo to a residue. Recrystallize the residue from acetone to give 6.69 g of the product.

Step B:

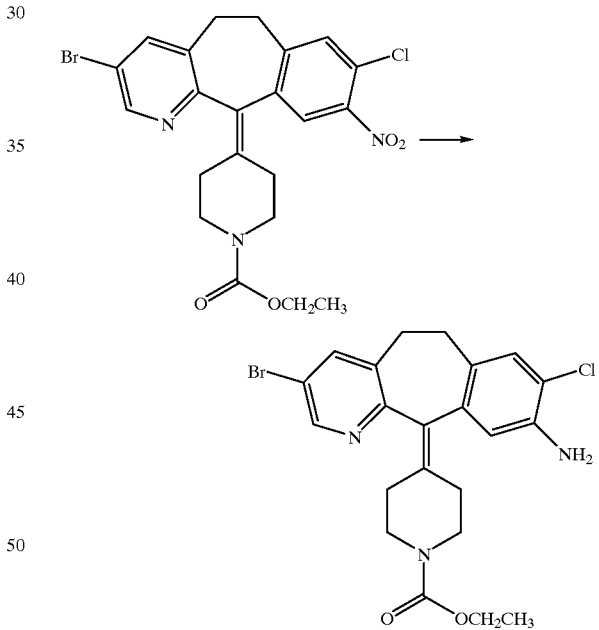

Combine 6.69 g (13.1 mmol) of the product of Step A and 100 mL of 85% EtOH/water, then add 0.66 g (5.9 mmol) of $CaCl_2$ and 6.56 g (1 17.9 mmol) of Fe and heat the mixture at reflux overnight. Filter the hot reaction mixture through Celite® and rinse the filter cake with hot EtOH. Concentrate the filtrate in vacuo to give 7.72 g of the product.

Step C:

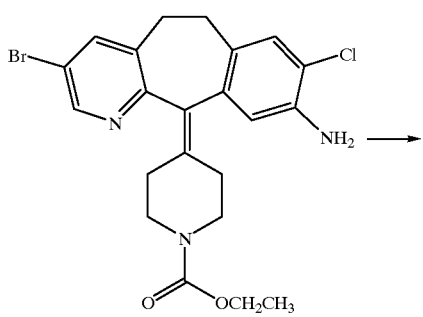

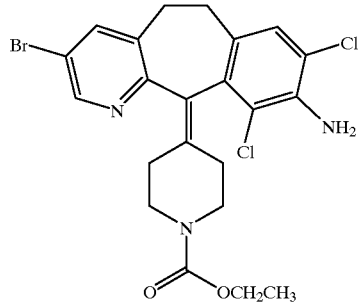

Dissolve 9.90 g (18.9 mmol) of the product of Step B, in 150 mL CH$_2$Cl$_2$ and 200 mL of CH$_3$CN and heat to 60° C. Add 2.77 g (20.8 mmol) N-chlorosuccinimide and heat to reflux for 3 h., monitoring the reaction by TCL (30%EtOAc/H$_2$O). Add an additional 2.35 g (10.4 mmol) of N-chlorosuccinimide and reflux an additional 45 min. Cool the reaction mixture to room temperature and extract with 1N NaOH and CH$_2$Cl$_2$. Dry the CH$_2$Cl$_2$ layer over MgSO$_4$, filter and purify by flash chromatography (1200 mL normal phase silica gel, eluting with 30% EtOAc/H$_2$O) to obtain 6.24 g of the desired product. M.p. 193–195.4° C.

Step D:

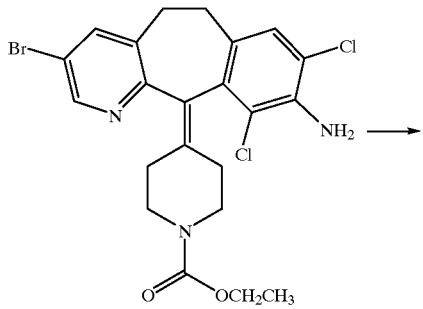

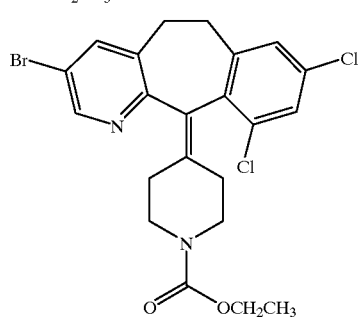

To 160 mL of conc. HCl at −10° C. add 2.07 g (30.1 mmol) NaNO$_2$ and stir for 10 min. Add 5.18 g (10.1 mmol) of the product of Step A and warm the reaction mixture from −10° C. to 0° C. for 2 h. Cool the reaction to −10° C., add 100 mL H$_3$PO$_2$ and let stand overnight. To extract the reaction mixture, pour over crushed ice and basify with 50% NaOH/CH$_2$Cl$_2$. Dry the organic layer over MgSO$_4$, filter and concentrate to dryness. Purify by flash chromatography (600 mL normal phase silica gel, eluting with 20% EtOAc/hexane) to obtain 3.98 g of product.

Step E:

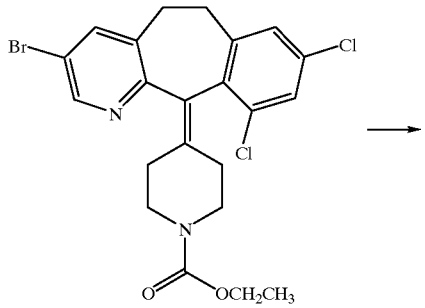

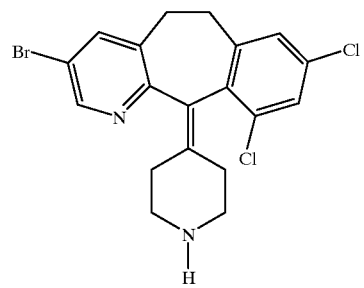

Dissolve 3.9 g of the product of Step D in 100 mL conc. HCl and reflux overnight. Cool the mixture, basify with 50% w/w NaOH and extract the resultant mixture with CH$_2$Cl$_2$. Dry the CH$_2$Cl$_2$ layer over MgSO$_4$, evaporate the solvent and dry under vacuum to obtain 3.09 g of the desired product.

Step F:

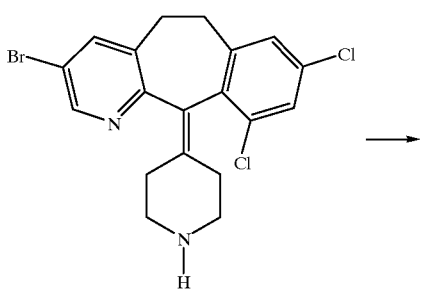

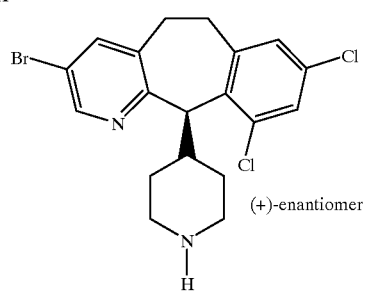

(+)-enantiomer

Using a procedure similar to that described in Preparative Example 8, obtain 1.73 g of the desired product, m.p. 169.6–170.1° C.; $[\alpha]_D^{25}$=+48.2° (c=1, MeOH). MH$^+$=425.

PREPARATIVE EXAMPLE 11

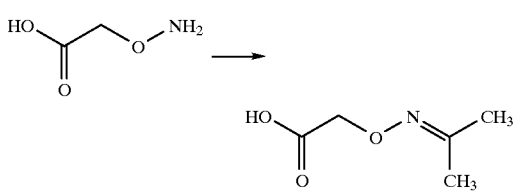

Follow the procedure outlined in Collect. Czech. Chem. Comm. (1990) 55, 2086. Dissolve 0.2 g (0.915 mmol) of (aminooxy)acetic acid hemihydrochloride (Aldrich) and 0.2 g (3 mmol) of acetone in 2 mL of pyridine and allow to stand for 18 hr. Concentrate under vacuum and partition the residue between ethyl acetate and 1N HCl. Dry the organic layer over magnesium sulfate and concentrate under vacuum to give a white solid mp=77.3–78° C.

PREPARATIVE EXAMPLE 12

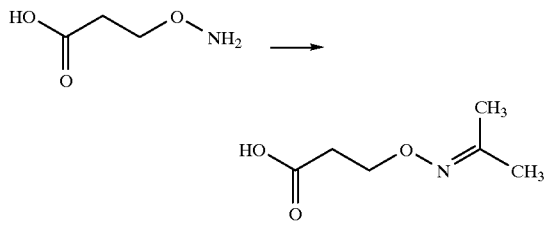

Follow the procedure of Preparative Example 11 but use 2-aminooxypropionic acid hemihydrochloride (Aldrich) instead of (aminooxy)acetic acid to obtain the product as a colorless oil.

PREPARATIVE EXAMPLE 13

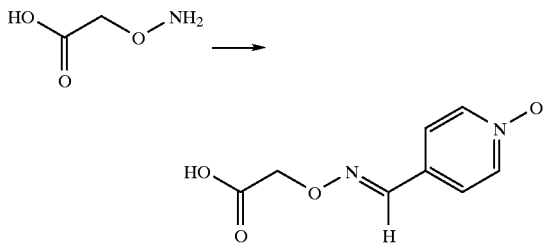

Follow the procedure of Preparative Example 11 but use 4-pyridinecarboxaldehyde N-oxide (Aldrich) instead of acetone to obtain the product that was recrystallized from water to give a white solid mp=227–228° C.

PREPARATIVE EXAMPLE 14

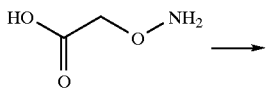

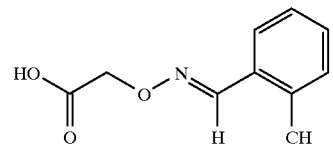

Follow the procedure of Preparative Example 11 but use 2-hydroxybenzaldehyde (Aldrich) instead of acetone to obtain the product as a white solid mp=152–153.5° C.

PREPARATIVE EXAMPLE 15

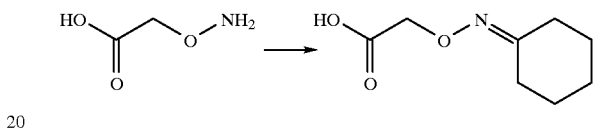

Follow the procedure of Preparative Example 11 but use cyclohexanone (Aldrich) instead of acetone to obtain the product as a white solid mp=97–98° C.

PREPARATIVE EXAMPLE 16

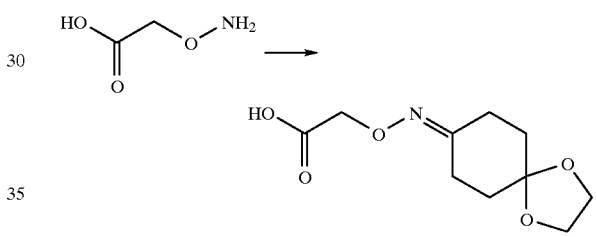

Follow the procedure of Preparative Example 11 but use 1,4-cyclohexandione mono-ethylene ketal (Aldrich) instead of acetone to obtain the product as a white solid mp=132–133° C.

PREPARATIVE EXAMPLE 17

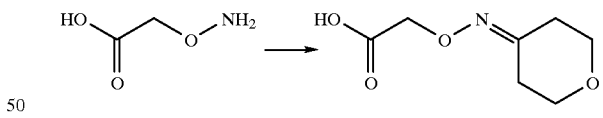

Follow the procedure of Preparative Example 11 but use tetrahydro-4H-pyran-4-one (Aldrich) instead of acetone to obtain the product as a white solid mp=107–108° C.

PREPARATIVE EXAMPLE 18

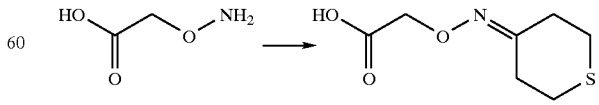

Follow the procedure of Preparative Example 11 but use tetrahydro-4H-thiopyran-4-one (Aldrich) instead of acetone to obtain the product as a white solid mp=141–143° C.

PREPARATIVE EXAMPLE 19

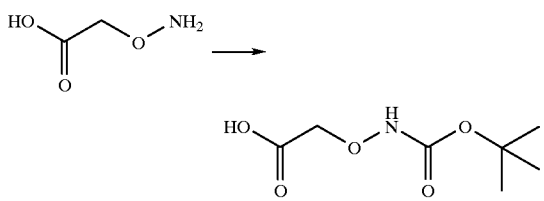

Dissolve 0.2 g (0.915 mmol) of (aminooxy)acetic acid hemihydrochloride (Aldrich) in 2 mL of 1N aqueous sodium hydroxide. Add a solution of 0.2 g (0.915 mmol) di-tert-butyldicarbonate (Aldrich) in 2 mL of methanol and stir for 24 hr. Cool to 0° C. and adjust to pH 5–6 with 1N HCl. Extract with four 20 mL portions of ethyl acetate. Dry the combined organic layers over magnesium sulfate and concentrate under vacuum to give 0.17 g of the product as a colorless oil that crystallized upon standing, mp=116–119° C.

ASSAYS

1. In vitro emzyme assays: FPT $IC_{50}$ (inhibition of farnesyl protein transrerase, in vitro enzyme assay) are determined by the methods disclosed in WO/10515 or WO 95/10516. The data demonstrate that the compounds of the invention are inhibitors of Ras-CVLS farnesylation by partially purified rat brain farnesyl protein transferase (FPT). The data also show that there are compounds of the invention which can be considered as potent ($IC_{50}<10$ $\mu$M) inhibitors of Ras-CVLS farnensylation by partially purified rat brain FPT.

2. Cell-based assay. COS $IC_{50}$ values refer to the COS cells activity inhibition of Ras processing, are determined by the methods disclosed in WO/10515 or WO 95/10516.

| Example No. | H-ras FPT $IC_{50}$ ($\mu$M) |
|---|---|
| 1 | 0.0270 |
| 2 | 0.0065 |
| 3 | 0.1800 |
| 4 | 0.0540 |
| 5 | 0.1700 |
| 6 | 0.0036 |
| 7 | 0.3700 |
| 8 | >0.1800 |
| 9 | 0.1500 |
| 10 | 0.0350 |
| 11 | 0.0240 |
| 12 | 0.0120 |
| 13 | 0.0130 |
| 14 | 0.0310 |
| 15 | 0.0320 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A—TABLETS

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|    | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B—CAPSULES

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|    | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

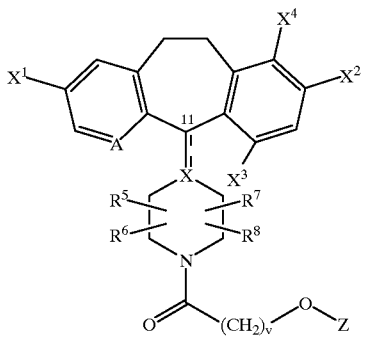

(1.0)

or a pharmaceutically acceptable salt or solvate thereof, wherein:

A represents N or N-oxide;

X represents CH or C, such that when X is CH, there is a single bond to carbon atom 11 as represented by the solid line; or when X is C, there is a double bond to carbon atom 11, as represented by the solid and dotted lines;

$X^1$ and $X^2$ are independently selected from bromo, iodo or chloro;

$X^3$ and $X^4$ are independently selected from bromo, iodo, chloro or hydrogen provided only one of $X^3$ or $X^4$ is hydrogen;

$R^5$, $R^6$, $R^7$ and $R^8$ each independently represents hydrogen, alkyl, aryl, or —$CONR^{40}R^{41}$ wherein $R^{40}$ and $R^{41}$ independently represent hydrogen, alkyl, alkoxy, aryl, aralkyl, heteroaryl, heteroarylalkyl, cycloalkyl, cycloalkylalkyl, heterocycloalkyl and heterocycloalkylalkyl, and further wherein $R^5$ may be combined with $R^6$ to represent =O or =S and/or $R^7$ may be combined with $R^8$ to represent =O or =S;

v is 1, 2, 3, 4, 5 or 6; and

Z represents —$NR^{19}R^{20}$ or —$N=CR^{19}R^{20}$; wherein $R^{19}$ and $R^{20}$ are independently selected from hydrogen, alkyl, alkoxy, aryl, aralkyl, heteroaryl, heteroarylalkyl, cycloalkyl, cycloalkylalkyl, heterocycloalkyl, heterocycloalkylalkyl, —$CONR^{10}R^{12}$, —$COOR^{10}$, —$COR^{10}$, —$SO_2R^{10}$ and —$SO_2NR^{10}R^{12}$, or $R^{19}$ and $R^{20}$ taken together form a cycloalkyl of 5–7 carbon atoms or a heterocycloalkyl ring containing 4–6 carbon atoms, wherein $R^{10}$ and $R^{12}$ are independently selected from hydrogen, alkyl, alkoxy, aryl, aralkyl, heteroaryl, heteroarylalkyl, cycloalkyl, cycloalkylalkyl, heterocycloalkyl or heterocycloalkylalkyl.

2. The compound of claim 1 wherein there is a single bond at carbon atom 11, X is CH and $R^5$, $R^6$, $R^7$ and $R^8$ are hydrogen.

3. The compound of claim 2 wherein $X^1$, $X^2$ and $X^3$ are bromo or chloro and $X^4$ is hydrogen.

4. The compound of claim 3 wherein v is one or two; and Z is —$NR^{19}R^{20}$ or —$N=CR^{19}R^{20}$ wherein $R^{19}$ and $R^{20}$ are independently selected from hydrogen, alkyl, aryl, heteroaryl, —$COR^{10}$ or —$COOR^{10}$ wherein $R^{10}$ is hydrogen or alkyl, or $R^{19}$ and $R^{20}$ taken together form a cycloalkyl or a heterocycloalkyl ring.

5. The compound of claim 4 wherein $R^{20}$ is aryl and the aryl ring is substituted with alkoxy, hydroxy or halo.

6. The compound of claim 4 wherein $R^{19}$ and $R^{20}$ taken together form a cycloalkyl ring and the cycloalkyl ring is substituted with heterocycloalkyl.
7. The compound of claim 1 which is any one of the following
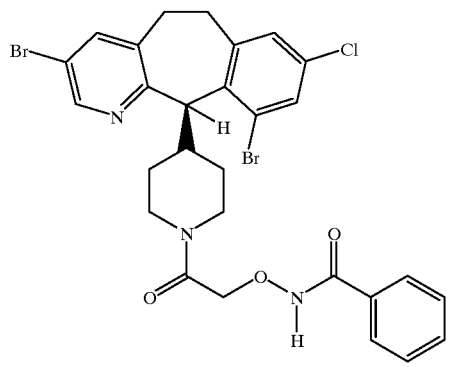
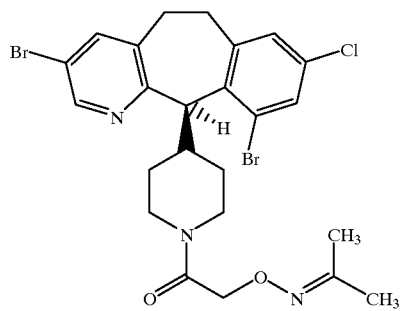
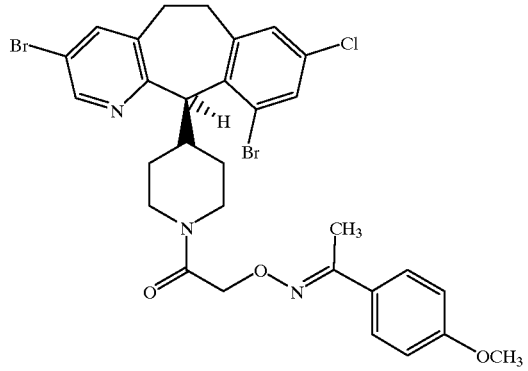
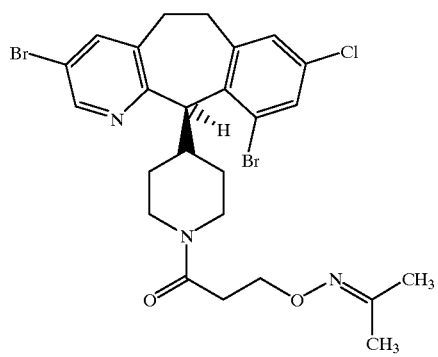
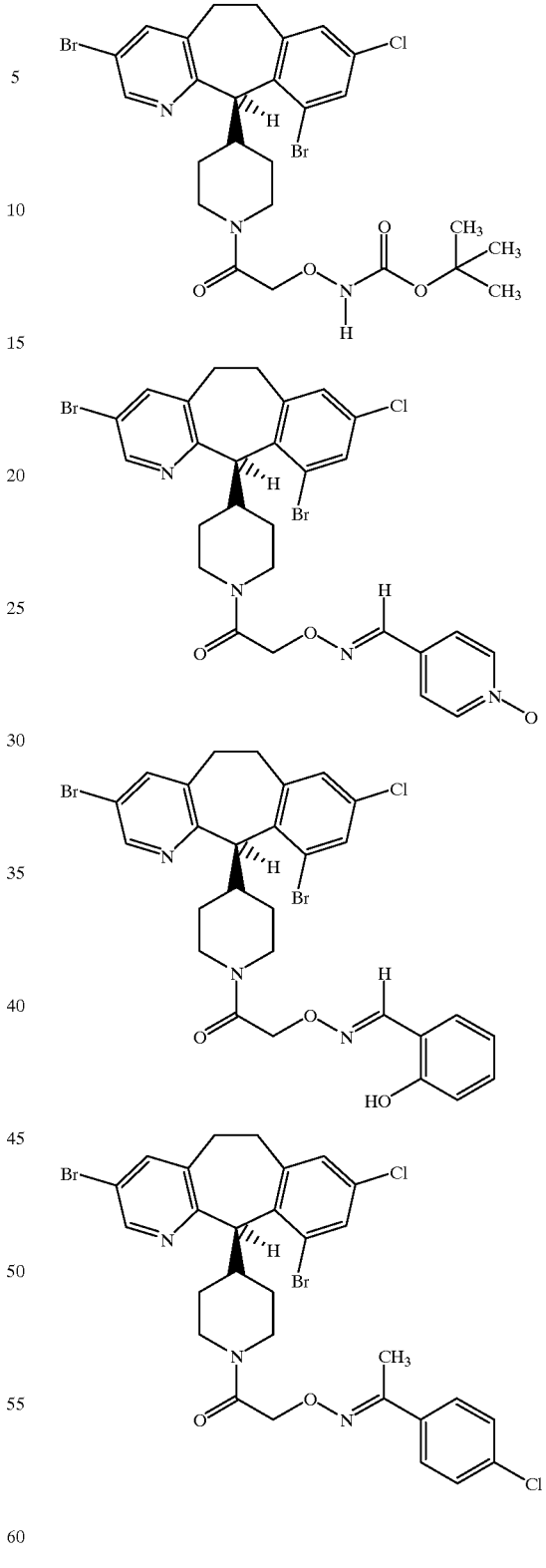

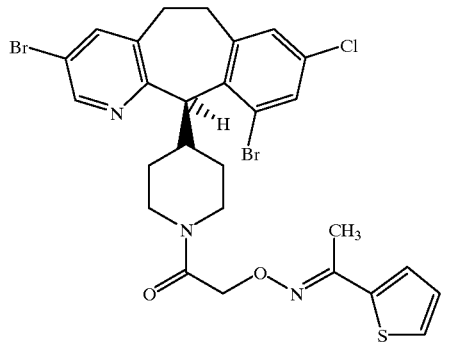
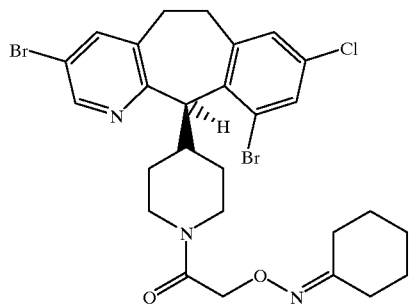
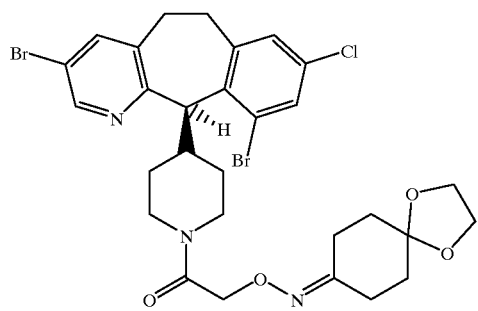
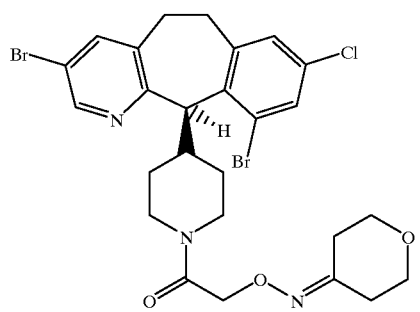
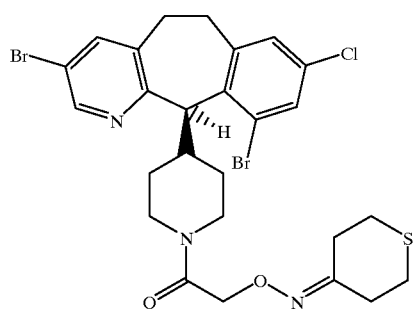
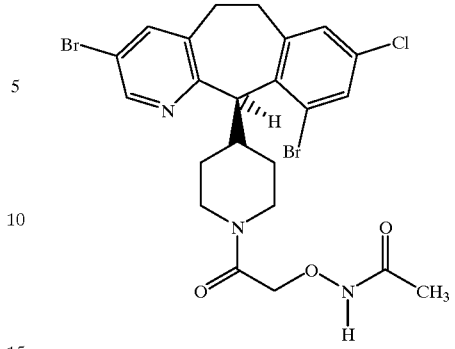
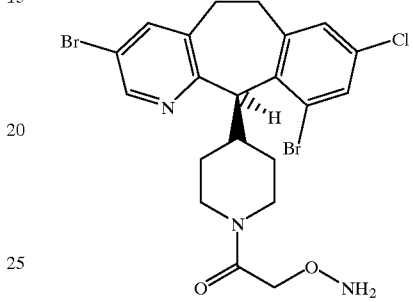
8. The compound of claim 1 which is
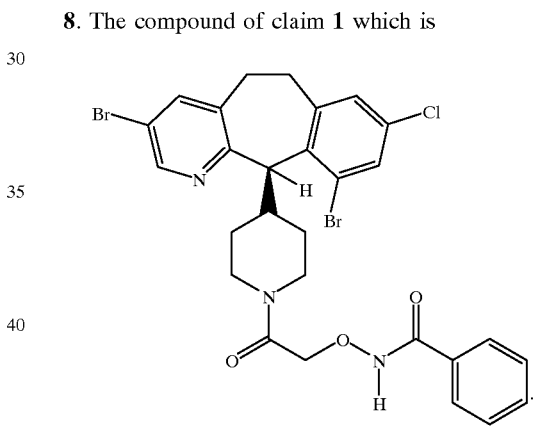
9. A pharmaceutical composition comprising an effective amount of compound of claim 1 in combination with a pharmaceutically acceptable carrier.
10. The compound of claim 1 which is
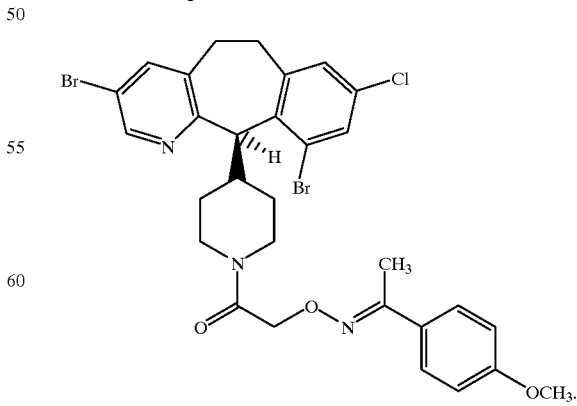

11. The compound of claim 1 which is
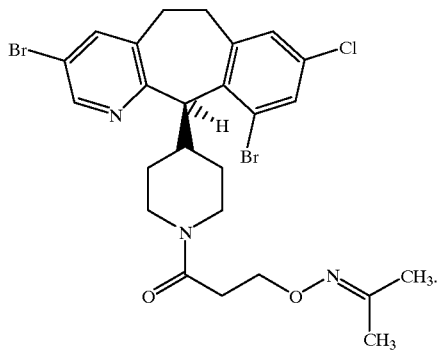
12. The compound of claim 1 which is
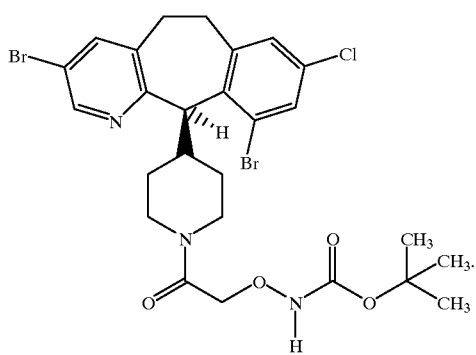
13. The compound of claim 1 which is
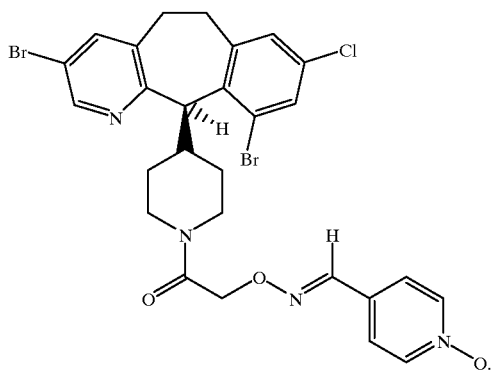
14. The compound of claim 1 which is
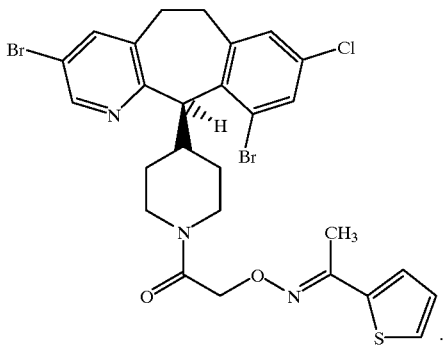
15. The compound of claim 1 which is
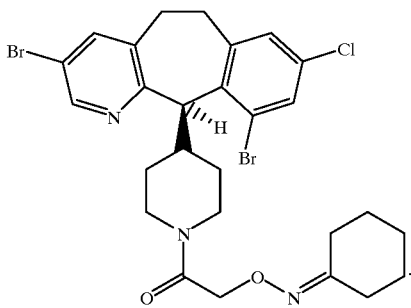
16. The compound of claim 1 which is
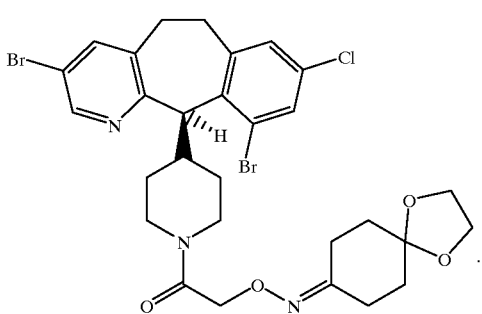

17. The compound of claim 1 which is

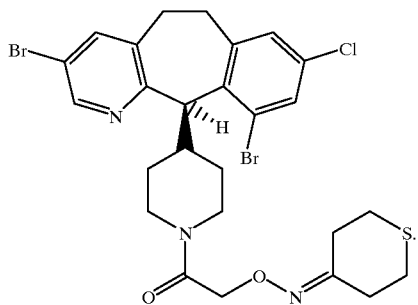

18. The compound of claim 1 which is

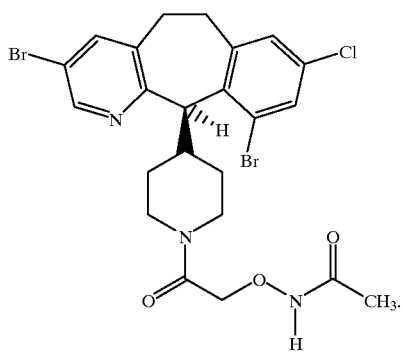

19. The compound of claim 1 which is

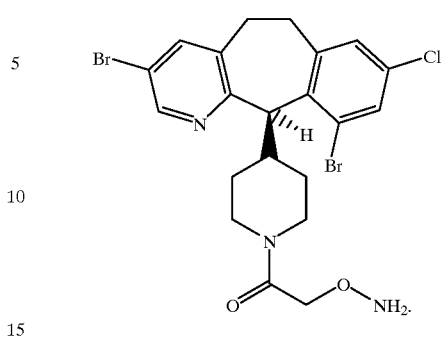

20. A method for inhibiting the abnormal growth of tumor cells expressing an activated ras oncogene by inhibition of ras farnesyl protein transferase in a mammal comprising administering to a mammal in need thereof an effective amount of a compound of claim 1.

21. The method of claim 20 wherein the cells inhibited are pancreatic tumor cells, lung cancer cells, myeloid leukemia tumor cells, thyroid follicular tumor cells, myelodysplastic tumor cells, epidermal carcinoma tumor cells, bladder carcinoma tumor cells or prostate tumor cells, breast tumor cells or colon tumors cells.

* * * * *